US011555020B2

(12) United States Patent
Galan et al.

(10) Patent No.: US 11,555,020 B2
(45) Date of Patent: Jan. 17, 2023

(54) SUBSTITUTED NAPHTHYL P38α MITOGEN-ACTIVATED PROTEIN KINASE INHIBITORS

(71) Applicant: GEN1E LIFESCIENCES INC., Palo Alto, CA (US)

(72) Inventors: Adam Galan, Alameda, CA (US); Wendy Luo, Palo Alto, CA (US); Ritu Lal, Palo Alto, CA (US)

(73) Assignee: GEN1E LIFESCIENCES INC., Palo Alto, CA (US)

( * ) Notice: Subject to any disclaimer, the term of this patent is extended or adjusted under 35 U.S.C. 154(b) by 0 days.

(21) Appl. No.: 17/700,168

(22) Filed: Mar. 21, 2022

(65) Prior Publication Data

US 2022/0315543 A1  Oct. 6, 2022

Related U.S. Application Data

(60) Provisional application No. 63/164,664, filed on Mar. 23, 2021.

(51) Int. Cl.
*C07D 265/32* (2006.01)
*A61P 35/00* (2006.01)
*C07D 295/135* (2006.01)

(52) U.S. Cl.
CPC ............ *C07D 265/32* (2013.01); *A61P 35/00* (2018.01); *C07D 295/135* (2013.01)

(58) Field of Classification Search
None
See application file for complete search history.

(56) References Cited

U.S. PATENT DOCUMENTS

| | | | |
|---|---|---|---|
| 3,594,386 | A | 7/1971 | Regnier et al. |
| 6,462,074 | B1 | 10/2002 | Stolle et al. |
| 8,173,684 | B2 | 5/2012 | Kasahara et al. |
| 11,286,260 | B2 | 3/2022 | Galan et al. |
| 2005/0256133 | A1 | 11/2005 | Lesur et al. |
| 2007/0066616 | A1 | 3/2007 | Shapiro et al. |
| 2007/0208015 | A1 | 9/2007 | Gill et al. |
| 2010/0215618 | A1 | 8/2010 | Carter et al. |
| 2015/0357549 | A1 | 12/2015 | Muller et al. |
| 2019/0151324 | A1 | 5/2019 | Shapiro et al. |

FOREIGN PATENT DOCUMENTS

| | | |
|---|---|---|
| CN | 101675034 A | 3/2010 |
| CN | 105308004 A | 2/2016 |
| CN | 109640970 A | 4/2019 |
| DE | 19801646 A1 | 7/1999 |
| EP | 3474835 A1 | 5/2019 |
| JP | 2007-532615 | 11/2007 |
| JP | 2010-180234 | 8/2010 |
| JP | 2011-513288 | 4/2011 |
| WO | 2004/065351 A1 | 8/2004 |
| WO | 2004/072077 A1 | 8/2004 |
| WO | 2005/100338 A1 | 10/2005 |
| WO | 2009/106844 A1 | 9/2009 |
| WO | 2010/082912 A1 | 7/2010 |
| WO | 2010/094977 A1 | 8/2010 |
| WO | 2015/121660 A1 | 8/2015 |
| WO | 2016/051155 | 4/2016 |
| WO | 2016/073633 | 5/2016 |
| WO | 2017/223284 A1 | 12/2017 |
| WO | 2020/118194 | 6/2020 |
| WO | 2021/183970 | 9/2021 |

OTHER PUBLICATIONS

International Search Report and Written Opinion for Application No. PCT/US2021/055950, dated Dec. 14, 2021, 14 pages.
Caira, Mino R. "Crystalline Polymorphism of Organic Compounds", Topics in Current Chemistry, Jan. 1998, vol. 198, pp. 163-208.
Kheiri et al., "Role pf p38/MAPKs in Alzheimer's disease: implications for amyloid beta toxicity targeted therapy", Reviews in Neuroscience, 2018, vol. 30, No. 1, pp. 9-30.
Mavropoulos et al., "p38 mitogen-activated protein kinase (p38 MAPK)-mediated autoimmunity: Lessons to learn from ANCA vasculitis and pemphigus vulgaris", Autoimmunity Reviews, Mar. 2013, vol. 12, Issue 5, pp. 580-590.
Nagao et al., "Synthesis and structure-activity relationships of novel, potent, orally active hypoxia-inducible factor-1 inhibitors", Bioorganic & Medicinal Chemistry, Jul. 2014, vol. 22, No. 19, pp. 5513-5529.
Segales et al., "Regulation of Muscle Stem Cell Functions: A Focus on the p38 MARK Signaling Pathway", Frontiers in Cell and Developmental Biology, Aug. 2016, vol. 4, Article 91, 15 pages.
Yong et al., "The p38 MAPK inhibitors for the treatment of inflammatory diseases and cancer", Expert Opinion on Investigational Drugs, Oct. 2009, ISSN 1354-3784, vol. 18, No. 12, pp. 1893-1905.
Chemical Abstract STN Registry Database Record for RN 851167-79-8, Entered STN May 26, 2005.
Chemical Abstract STN Registry Database Record for RN 2331174-12-8, Entered STN Jun. 12, 2019.
Chemical Abstract STN Registry Database Record for RN 2338713-47-7, Entered STN Jun. 18, 2019.
Chemical Abstract STN Registry Database Record for RN 2347052-15-5, Entered STN Jun. 27, 2019.
Cheng et al., "Identification and Optimization of New Dual Inhibitors of B-Raf and Epidermal Growth Factor Receptor Kinases for Overcoming Resistance against Vemurafenib", Journal of Medicinal Chemistry, American Chemical Society, 2014, vol. 57, pp. 2692-2703.
Chemical Abstract STN Registry Database, Record for RN 1587574-74-0, "N-[4-[(4-Chlorobenzoyl)amino]phenyl]-2-oxo-1-piperazineacetamide hydrochloride", entered on Apr. 21, 2014.
Wang et al., "Chapter 2—A Structural Atlas of Kinases Inhibited by Clinically Approved Drugs", Methods of Enzymology, 2014, vol. 548, pp. 23-67.
International Search Report and Written Opinion for Application No. PCT/US2019/064960, dated Feb. 25, 2020, 7 pages.

(Continued)

*Primary Examiner* — Brian J Davis

(57) ABSTRACT

Substituted naphthyl p38α mitogen-activated protein kinase inhibitors, pharmaceutical compositions thereof, and the use of the substituted naphthyl p38α mitogen-activated protein kinase inhibitors and pharmaceutical compositions thereof for treating diseases are disclosed.

22 Claims, 1 Drawing Sheet

Specification includes a Sequence Listing.

(56) References Cited

OTHER PUBLICATIONS

International Search Report and Written Opinion for Application No. PCT/US2017/038697, dated Oct. 31, 2017, 12 pages.
International Search Report and Written Opinion for Application No. PCT/US2021/032487, dated Sep. 22, 2021, 19 pages.
Extended European Search Report for Application No. EP 17816192, dated Mar. 30, 2020, 5 pages.
Non-Final Office Action for U.S. Appl. No. 16/312,499, dated Feb. 13, 2020, 8 pages.
Final Office Action for U.S. Appl. No. 16/312,499, dated May 21, 2020, 11 pages.
Non-Final Office Action for U.S. Appl. No. 17/231,598, dated Jun. 29, 2021, 9 pages.
Non-Final Office Action for U.S. Appl. No. 16/872,114, dated Dec. 7, 2020, 7 pages.
Biava et al., "Synthesis and Antimycobacterial Activity of New Amidoderivatives of Ortho-, Meta- and Para-Toluidine", Medicinal Chemistry Research, Jan. 1998, vol. 8, No. 9, pp. 523-541.
Biava et al., "Antimycobacterial activity of new ortho-, meta- and para-toluidine derivatives", II Farmaco, 1999, vol. 54, pp. 721-727.
Chemical Abstract STN Registry Database record for RN 2337349-33-2, entered into STN Jun. 17, 2019.
Chemical Abstract STN Registry Database Record for RN 1293859-67-2, STN Entered May 12, 2011.
Haller et al., "An updated patent review of p38 MAP kinase inhibitors (2014-2019)", Expert Opinion on Therapeutics Patents, 2020, vol. 30, No. 6, p. 453-466.
Koroleva et al., "Synthesis of new amides of the N-methylpiperazine series", Russian Journal of Organic Chemistry, Nauka/Interperiodica, Nov. 2011, vol. 47, No. 10, pp. 1556-1563.
Lee et al., "Docketing-based 3D-QSAR study for 11β-HSD1 inhibitors", Bioorganic & Medicinal Chemistry Letters, 2008, vol. 18, pp. 2479-2490.
Pubchem CID 899207 created Jul. 9, 2005, accessed on Feb. 5, 2020, 9 pages.
Pubchem, Substance Database SID 105140242, available on Feb. 22, 2011, retrieved on Aug. 8, 2017, retrieved from https://pubchem.ncbi.nlm.nih.gov/substance/105140242.
Sasindran et al., "Mycobacterium Tuberculosis Infection and Inflammation: what is Beneficial for the Host and for the Bacterium?", Frontiers in Microbiology, Jan. 2011, vol. 2, Article 2, 33 pages.
Shah et al., "Novel Noncatalytic Substrate-Selective p38[alpha]-Specific MAPK Inhibitors with Endothelial-Stabilizing and Anti-Inflammatory Activity", The Journal of Immunology, Mar. 2017, vol. 198, No. 8, pp. 3296-3306.
Chemical Abstract STN Registry Database Record for RN 2337349-33-2, [online] retrieved from STN Registry Database [retrieved on Jun. 17, 2019].
Chemical Abstract STN Registry Database Record for RN 255713-96-3, [online] retrieved from STN Registry Database [retrieved on Feb. 10, 2000].
Chemical Abstract STN Registry Database Record for RN 697229-25-7, [online] retrieved from STN Registry Database [retrieved on Jun. 22, 2004].
International Search Report and Written Opinion for Application No. PCT/US2022/021181, dated Jun. 28, 2022, 15 pages.

SUBSTITUTED NAPHTHYL P38α MITOGEN-ACTIVATED PROTEIN KINASE INHIBITORS

This application claims the benefit under 35 U.S.C. § 119(e) of U.S. Provisional Application No. 63/164,664 filed on Mar. 23, 2021, which is incorporated by reference in its entirety.

FIELD

The present disclosure relates to substituted naphthyl p38α mitogen-activated protein kinase inhibitors, pharmaceutical compositions thereof, and the use of the substituted naphthyl p38α mitogen-activated protein kinase inhibitors and pharmaceutical compositions thereof for treating diseases.

SEQUENCE LISTING

The instant application contains a Sequence Listing which has been submitted electronically in ASCII format and is hereby incorporated by reference in its entirety. The ASCII copy, created on Mar. 21, 2022, is named 67LZ-000610PC-349166_SL.txt and is 755 bytes in size.

BACKGROUND

Mitogen-activated protein kinases (MAPKs) are serine/threonine protein kinases that process and regulate cellular properties in response to a wide range of extracellular stimuli. These enzymes phosphorylate the OH group of serine or threonine in proteins and play important roles in the regulation of cell proliferation, differentiation, survival and apoptosis. In mammalian cells, several distinct MAPKs have been identified, including p38 MAPK.

p38 MAPKs are a class of MAPKs responsive to stress stimuli such as inflammatory cytokines and reactive oxygen species (ROS) and is involved in a wide range of signaling pathways that stimulate different biological functions. For example, p38 MAPK has been found to play an essential role in the regulation of pro-inflammatory signaling networks and in the biosynthesis of cytokines, including tumor necrosis factor-α (TNF-α) and interleukin-1β (IL-1β) in immune cells Studies have shown that p38 MAPKs contribute to the pathogenesis of chronic inflammation, leading to preclinical or clinical trials for the application of p38 MAPK inhibitors in inflammatory diseases such as rheumatoid arthritis and asthma.

p38 MAPKs comprise four isoforms (α, β, γ and δ). p38α MAPK was the first isoform of p38 MAPK to be identified and was first recognized as a stress-induced kinase that can be activated by lipopolysaccharide (LPS) and inflammatory cytokines. Inhibition of p38 MAPK has been shown to effectively alleviate the symptoms of inflammatory diseases such as rheumatoid arthritis, cardiovascular disease, and inflammatory pain.

Many p38 MAPK catalytic inhibitors are poorly effective and cause toxicity possibly due to activity against non-inflammatory p38 and loss of p38α-dependent counterregulatory responses. p38α MAPK inhibitors that can selectively block certain p38α MAPK functions and preserve critical counterregulatory and homeostatic functions with application for the treatment of inflammatory and oncologic diseases are desired.

SUMMARY

According to the present invention, a compound has the structure of Formula (6):

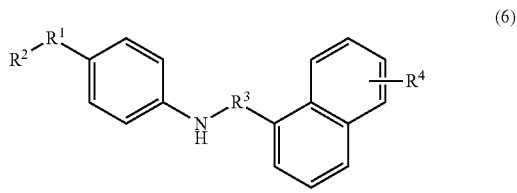

or a pharmaceutically acceptable salt thereof, wherein,
$R^1$ is selected from $C_{1-4}$ alkanediyl, $C_{1-4}$ heteroalkanediyl, substituted $C_{1-4}$ alkanediyl, and substituted $C_{1-4}$ heteroalkanediyl;
$R^2$ is substituted $C_{5-8}$ heterocycloalkyl;
$R^3$ is selected from —C(=O)— and —S(=O)$_2$—; and
$R^4$ is selected from —N($R^5$)$_2$ wherein each $R^5$ is independently selected from hydrogen and $C_{1-4}$ alkyl.

According to the present invention pharmaceutical compositions comprise a compound according to the present invention or a pharmaceutically acceptable salt thereof.

According to the present invention, methods of treating a disease in a patient comprise administering to a patient in need of such treatment a therapeutically effective amount of a compound according to the present invention or a pharmaceutically acceptable salt thereof, wherein the disease is treated by inhibiting the p38α MAPK receptor.

BRIEF DESCRIPTION OF THE DRAWINGS

The drawings described herein are for illustration purposes only. The drawings are not intended to limit the scope of the present disclosure.

DETAILED DESCRIPTION

Figure 1:
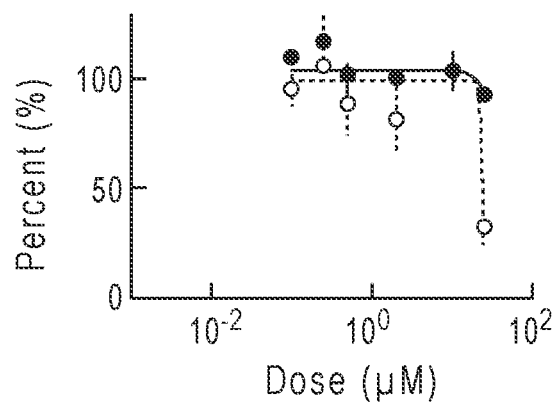
FIG. 1 shows the cell viability (black) and IC$_{50}$ (red) curves for a SARS-CoV-2 cell line treated with Compound (4).

A dash ("-") that is not between two letters or symbols is used to indicate a point of attachment for a moiety or substituent. For example, —CONH$_2$ is attached through the carbon atom.

"Alkyl" refers to a saturated, branched, or straight-chain, monovalent hydrocarbon radical derived by the removal of one hydrogen atom from a single carbon atom of a parent alkane, alkene, or alkyne. Examples of alkyl groups include methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like. The term "alkyl" includes groups having any degree or level of saturation, i.e., groups having exclusively carbon-carbon single bonds, groups having one or more carbon-carbon double bonds, groups having one or more carbon-carbon triple bonds, and groups having combinations of carbon-carbon single, double, and triple bonds. Where a specific level of saturation is intended, the terms alkanyl, alkenyl, and alkynyl are used. An alkyl group can be $C_{1-6}$ alkyl, $C_{1-5}$ alkyl, $C_{1-4}$ alkyl, $C_{1-3}$ alkyl, ethyl or methyl.

"Alkoxy" refers to a radical —OR where R is alkyl as defined herein. Examples of alkoxy groups include methoxy, ethoxy, propoxy, and butoxy. An alkoxy group can be $C_{1-6}$ alkoxy, $C_{1-5}$ alkoxy, $C_{1-4}$ alkoxy, $C_{1-3}$ alkoxy, ethoxy or methoxy.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms selected from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like. An aryl group can be $C_{6-10}$ aryl, $C_{6-9}$ aryl, $C_{6-8}$ aryl, or phenyl. Aryl, however, does not encompass or overlap in any way with heteroaryl, separately defined herein.

"Arylalkyl" refers to an acyclic alkyl radical in which one of the hydrogen atoms bonded to a carbon atom is replaced with an aryl group. Examples of arylalkyl groups include benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, or arylalkynyl is used. An arylalkyl group can be $C_{7-16}$ arylalkyl, e.g., the alkanyl, alkenyl or alkynyl moiety of the arylalkyl group is $C_{1-6}$ and the aryl moiety is $C_{6-10}$. An arylalkyl group can be $C_{7-16}$ arylalkyl, e.g., the alkanyl, alkenyl or alkynyl moiety of the arylalkyl group is $C_{1-6}$ and the aryl moiety is $C_{6-10}$. An arylalkyl group can be $C_{7-9}$ arylalkyl, where the alkyl moiety can be $C_{1-3}$ alkyl and the aryl moiety can be phenyl. An arylalkyl group can be $C_{7-16}$ arylalkyl, $C_{7-14}$ arylalkyl, $C_{7-12}$ arylalkyl, $C_{7-10}$ arylalkyl, $C_{7-8}$ arylalkyl, or benzyl.

"Bioavailability" refers to the rate and amount of a drug that reaches the systemic circulation of a patient following administration of the drug or prodrug thereof to the patient and can be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or form of drug to the patient, and $T_{max}$ is the time to the maximum concentration ($C_{max}$) of a drug in the plasma or blood of a patient following administration of a dose of the drug or form of drug to the patient.

"Oral bioavailability" (F %) refers to the fraction of an oral administered drug that reaches systemic circulation. Oral bioavailability is a product of fraction absorbed, fraction escaping gut-wall elimination, and fraction escaping hepatic elimination; and the factors that influence bioavailability can be divided into physiological, physicochemical, and biopharmaceutical factors.

"Compounds" and moieties disclosed herein include any specific compounds within the disclosed formula. Compounds may be identified either by chemical structure and/or by chemical name. Compounds are named using the ChemBioDraw Professional 17.1.0.105 (9) (CambridgeSoft, Cambridge, Mass.) nomenclature program. When the chemical structure and chemical name conflict, the chemical structure is determinative of the identity of the compound. The compounds described herein may comprise one or more stereogenic centers and/or double bonds and therefore may exist as stereoisomers such as double-bond isomers (i.e., geometric isomers), enantiomers, diastereomers, or atropisomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled in the art.

Compounds and moieties disclosed herein include optical isomers of compounds and moieties, racemates thereof, and other mixtures thereof. In such embodiments, the single enantiomers or diastereomers may be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column with chiral stationary phases. In addition, compounds include (Z)- and (E)-forms (or cis- and trans-forms) of compounds with double bonds either as single geometric isomers or mixtures thereof.

Compounds and moieties may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms. Certain compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing.

"Cycloalkyl" refers to a saturated or partially unsaturated cyclic alkyl radical. A cycloalkyl group can be $C_{3-8}$ cycloalkyl, $C_{3-5}$ cycloalkyl, $C_{5-6}$ cycloalkyl, cyclopropyl, cyclopentyl, or cyclohexyl. A cycloalkyl can be selected from cyclopropyl, cyclobutyl, cyclopentyl, cyclohexyl, cycloseptyl, and cyclooctyl.

"Cycloalkylalkyl" refers to an acyclic alkyl radical in which one of the hydrogen atoms bonded to a carbon atom is replaced with a cycloalkyl group as defined herein. Where specific alkyl moieties are intended, the nomenclature cycloalkylalkyl, cycloalkylalkenyl, or cycloalkylalkynyl is used. A cycloalkylalkyl group can be $C_{4-30}$ cycloalkylalkyl, e.g., the alkanyl, alkenyl, or alkynyl moiety of the cycloalkylalkyl group is $C_{1-10}$ and the cycloalkyl moiety of the cycloalkylalkyl moiety is $C_{3-20}$. A cycloalkylalkyl group can be $C_{4-20}$ cycloalkylalkyl, e.g., the alkanyl, alkenyl, or alkynyl moiety of the cycloalkylalkyl group is $C_{1-8}$ and the cycloalkyl moiety of the cycloalkylalkyl group is $C_{3-12}$. A cycloalkylalkyl can be $C_{4-9}$ cycloalkylalkyl, wherein the alkyl moiety of the cycloalkylalkyl group is $C_{1-3}$ alkyl, and the cycloalkyl moiety of the cycloalkylalkyl group is $C_{3-6}$ cycloalkyl. A cycloalkylalkyl group can be $C_{4-12}$ cycloalkylalkyl, $C_{4-10}$ cycloalkylalkyl, $C_{4-8}$ cycloalkylalkyl, and $C_{4-6}$ cycloalkylalkyl. A cycloalkylalkyl group can be cyclopropylmethyl (—$CH_2$-cyclo-$C_3H_5$), cyclopentylmethyl (—$CH_2$-cyclo-$C_5H_9$), or cyclohexylmethyl (—$CH_2$-cyclo-$C_6H_{11}$). A cycloalkylalkyl group can be cyclopropylethenyl (—CH=CH-cyclo-$C_3H_5$), cyclopentylethynyl (—C≡C-cyclo-$C_5H_9$), or the like.

"Cycloalkylheteroalkyl" by itself or as part of another substituent refers to a heteroalkyl group in which one or more of the carbon atoms (and certain associated hydrogen atoms) of an alkyl group are independently replaced with the same or different heteroatomic group or groups and in which one of the hydrogen atoms bonded to a carbon atom is replaced with a cycloalkyl group. Where specific alkyl moieties are intended, the nomenclature cycloalkylheteroalkanyl, cycloalkylheteroalkenyl, and cycloalkylheteroalkynyl is used. In a cycloalkylheteroalkyl, the heteroatomic group can be selected from —O—, —S—, —NH—, —N(—$CH_3$)—, —SO—, —$SO_2$—, —Si—, —B—, or the heteroatomic group can be selected from —O— and —NH—, or the heteroatomic group is —O— or —NH—.

"Cycloalkyloxy" refers to a radical —OR where R is cycloalkyl as defined herein. Examples of cycloalkyloxy groups include cyclopropyloxy, cyclobutyloxy, cyclopentyloxy, and cyclohexyloxy. A cycloalkyloxy group can be $C_{3-6}$ cycloalkyloxy, $C_{3-5}$ cycloalkyloxy, $C_{5-6}$ cycloalkyloxy, cyclopropyloxy, cyclobutyloxy, cyclopentyloxy, or cyclohexyloxy.

"Disease" refers to a disease, disorder, condition, or symptom of any of the foregoing.

"Drug" as defined under 21 U.S.C. § 321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . . .".

"Halogen" refers to a fluoro, chloro, bromo, or iodo group.

"Heteroalkoxy" refers to an alkoxy group in which one or more of the carbon atoms are replaced with a heteroatom. A heteroalkoxy group can be $C_{1-6}$ heteroalkoxy, $C_{1-5}$ heteroalkoxy, $C_{1-4}$ heteroalkoxy, or $C_{1-3}$ heteroalkoxy. In a heteroalkoxy, the heteroatomic group can be selected from —O—, —S—, —NH—, —NR— where R is $C_{1-6}$ alkyl, —SO—, —$SO_2$—, —Si—, and —B—, or the heteroatomic group can be selected from —O— and —NH—, or the heteroatomic group is —O— and —NH—. A heteroalkoxy group can be $C_{1-6}$ heteroalkoxy, $C_{1-5}$ heteroalkoxy, $C_{1-4}$ heteroalkoxy, or $C_{1-3}$ heteroalkoxy.

"Heteroalkyl" by itself or as part of another substituent refer to an alkyl group in which one or more of the carbon atoms (and certain associated hydrogen atoms) are independently replaced with the same or different heteroatomic group or groups. Examples of heteroatomic groups include —O—, —S—, —Si—, —B—, —NH—, —NR—, —O—O—, —S—S—, =N—N=, —N=N—, —N=N—NR—, —PR—, —P(O)OR—, —P(O)R—, —POR—, —SO—, —$SO_2$—, and —Sn(R)$_2$—, where each R is independently selected from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, and substituted $C_{7-18}$ heteroarylalkyl. Each R can be independently selected from hydrogen and $C_{1-3}$ alkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example, $C_{1-6}$ heteroalkyl includes groups having five carbon atoms and one heteroatom, groups having four carbon atoms and two heteroatoms. In a heteroalkyl, the heteroatomic group can be selected from —O—, —S—, —NH—, —N(—$CH_3$)—, —SO—, —$SO_2$—, —Si—, and —B—, or the heteroatomic group can be selected from —O— and —NH—, or the heteroatomic group can be —O— or —NH—. A heteroalkyl group can be $C_{1-6}$ heteroalkyl, $C_{1-5}$ heteroalkyl, or $C_{1-4}$ heteroalkyl, or $C_{1-3}$ heteroalkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which may be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. When the total number of N, S, and O atoms in the heteroaryl group exceeds one, the heteroatoms may or may not be adjacent to one another. The total number of heteroatoms in the heteroaryl group is not more than two. In a heteroaryl, the heteroatomic group can be selected from —O—, —S—, —NH—, —N(—$CH_3$)—, —SO—, —$SO_2$—, —Si—, and —B—, or the heteroatomic group can be selected from —O— and —NH—, or the heteroatomic group can be —O— or —NH—. A heteroaryl group can be selected from, for example, $C_{5-10}$ heteroaryl, $C_{5-9}$ heteroaryl, $C_{5-8}$ heteroaryl, $C_{5-7}$ heteroaryl, $C_{5-6}$ heteroaryl, $C_5$ heteroaryl or $C_6$ heteroaryl.

Examples of heteroaryl groups include groups derived from acridine, arsindole, carbazole, a-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, and oxazolidine. A heteroaryl groups can be derived, for example, from thiophene, pyrrole, benzothiophene, benzofuran, indole, pyridine, quinoline, imidazole, oxazole, or pyrazine. For example, a heteroaryl can be $C_5$ heteroaryl and can be selected from furyl, thienyl, pyrrolyl, imidazolyl, pyrazolyl, isothiazolyl, or isoxazolyl. A heteroaryl can be $C_6$ heteroaryl, and can be selected from pyridinyl, pyrazinyl, pyrimidinyl, and pyridazinyl.

"Heteroarylalkyl" refers to an arylalkyl group in which one of the carbon atoms (and certain associated hydrogen atoms) is replaced with a heteroatom. A heteroarylalkyl group can be C6-16 heteroarylalkyl, $C_{6-14}$ heteroarylalkyl, $C_{6-12}$ heteroarylalkyl, $C_{6-10}$ heteroarylalkyl, $C_{6-8}$ heteroarylalkyl, or $C_7$ heteroarylalkyl, or $C_6$ heteroarylalkyl. In a heteroarylalkyl, the heteroatomic group can be selected from —O—, —S—, —NH—, —N(—CH$_3$)—, —SO—, —SO$_2$—, —Si—, and —B—, or the heteroatomic group can be selected from —O— and —NH—, or the heteroatomic group can be —O— or —NH—.

"Heterobicycloalkyl" refers to a moiety having two heterocycloalkyl groups. A heterobicyclcyloalkyl group can be a fused ring or spiro compound.

"Heterocycloalkyl" by itself or as part of another substituent refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system violates the Hückel-rule. Examples of heteroatoms to replace the carbon atom(s) include N, P, O, S, B, and Si. Examples of heterocycloalkyl groups include groups derived from epoxides, azirines, thiiranes, imidazolidine, morpholine, piperazine, piperidine, pyrazolidine, pyrrolidine, and quinuclidine. A heterocycloalkyl can be $C_5$ heterocycloalkyl and is selected from pyrrolidinyl, tetrahydropyranyl, tetrahydrothiophenyl, imidazolidinyl, oxazolidinyl, thiazolidinyl, doxolanyl, and dithiolanyl. A heterocycloalkyl can be $C_6$ heterocycloalkyl and can be selected from piperidinyl, tetrahydropyranyl, piperizinyl, oxazinyl, dithianyl, and dioxanyl. A heterocycloalkyl group can be $C_{3-8}$ heterocycloalkyl, $C_{3-8}$ heterocycloalkyl, $C_{3-5}$ heterocycloalkyl, $C_{5-6}$ heterocycloalkyl, $C_5$ heterocycloalkyl or $C_6$ heterocycloalkyl. In a heterocycloalkyl, the heteroatomic group can be selected from —O—, —S—, —NH—, —N(—CH$_3$)—, —SO—, —SO$_2$—, —Si—, —B—, or the heteroatomic group can be selected from —O— and —NH—, or the heteroatomic group can be —O— or —NH—.

"Heterocycloalkylalkyl" refers to a cycloalkylalkyl group in which one or more carbon atoms (and certain associated hydrogen atoms) of the cycloalkyl ring are independently replaced with the same or different heteroatom. A heterocycloalkylalkyl can be $C_{4-12}$ heterocycloalkylalkyl, $C_{4-10}$ heterocycloalkylalkyl, $C_{4-8}$ heterocycloalkylalkyl, $C_{4-6}$ heterocycloalkylalkyl, $C_{6-7}$ heterocycloalkylalkyl, or $C_6$ heterocycloalkylalkyl or $C_7$ heterocycloalkylalkyl. In a heterocycloalkylalkyl, the heteroatomic group can be selected from —O—, —S—, —NH—, —N(CH$_3$)—, —SO—, —SO$_2$—, —Si—, —B—, or the heteroatomic group can be selected from —O— and —NH—, or the heteroatomic group can be —O— or —NH—.

"Parent aromatic ring system" refers to an unsaturated cyclic or polycyclic ring system having a cyclic conjugated π (pi) electron system with 4n+2 electrons (Hückel rule). Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like.

"Hydrates" refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism.

"Parent aromatic ring system" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of π-electrons corresponding to the Hückel rule (4n+2). Examples of heteroatoms to replace the carbon atoms include N, P, O, S, Si, and B. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and thiazolidine, oxazolidine.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of suitable inorganic acids include hydrochloric acid, hydrobromic acid, sulfuric acid, nitric acid, phosphoric acid, and the like. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A salt can be formed when one or more acidic protons present in the parent compound are replaced by a metal ion, e.g., an alkali metal ion, an alkaline earth ion, or an aluminum ion, or combinations thereof; or coordinates with an organic base such as ethanolamine, diethanolamine, triethanolamine, N-methylglucamine, and the like. A pharmaceutically acceptable salt can be the hydrochloride salt. A pharmaceutically acceptable salt can be the sodium salt. In compounds having two or more ionizable groups, a pharmaceutically acceptable salt can comprise one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound provided by the present disclosure or a pharmaceutically acceptable salt thereof and at least one pharmaceutically acceptable vehicle, with which the compound provided by the present disclosure or a pharmaceutically acceptable salt thereof is administered to a patient. Pharmaceutically acceptable vehicles are known in the art.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by administering a compound provided by the present disclosure in a preventative fashion. The application of a therapeutic agent for preventing or prevention of a disease of disorder is known as 'prophylaxis.' Compounds provided by the present disclosure can provide superior prophylaxis because of lower long-term side effects over long time periods.

"Solvate" refers to a molecular complex of a compound with one or more solvent molecules in a stoichiometric or non-stoichiometric amount. Such solvent molecules are those commonly used in the pharmaceutical arts, which are known to be innocuous to a patient, such as water or ethanol. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

"Solvates" refers to incorporation of solvents into to the crystal lattice of a compound described herein, in stoichiometric proportions, resulting in the formation of an adduct. Methods of making solvates include, for example, storage in an atmosphere containing a solvent, dosage forms that include the solvent, or routine pharmaceutical processing steps such as, for example, crystallization (i.e., from solvent or mixed solvents) vapor diffusion. Solvates may also be formed, under certain circumstances, from other crystalline solvates or hydrates upon exposure to the solvent or upon suspension material in solvent. Solvates may crystallize in more than one form resulting in solvate polymorphism.

"A compound provided by the present disclosure" refers to a compound encompassed by Formula (6) and pharmaceutically salts thereof. In certain embodiments, a compound provided by the present disclosure can further include a compound encompassed by Formula (6), pharmaceutically salts, solvates, hydrates, and/or prodrugs of any of the foregoing.

Compounds provided by the present disclosure also include crystalline and amorphous forms of the compounds, including, for example, polymorphs, pseudopolymorphs, solvates, hydrates, unsolvated polymorphs (including anhydrates), conformational polymorphs, and amorphous forms of the compounds, as well as mixtures thereof "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

"Substituted" refers to a group in which one or more hydrogen atoms are independently replaced with the same or different substituent(s). Each substituent can be independently selected from deuterio, halogen, —OH, —CN, —CF$_3$, —OCF$_3$, =O, —NO$_2$, C$_{1-6}$ alkoxy, C$_{1-6}$ alkyl, —COOR, —NR$_2$, and —CONR$_2$; wherein each R is independently selected from hydrogen and C$_{1-6}$ alkyl. Each substituent can be independently selected from deuterio, halogen, —NH$_2$, —OH, C$_{1-3}$ alkoxy, and C$_{1-3}$ alkyl, trifluoromethoxy, and trifluoromethyl. Each substituent can be independently selected from deuterio, —OH, methyl, ethyl, trifluoromethyl, methoxy, ethoxy, and trifluoromethoxy. Each substituent can independently be selected from deuterio, $C_{1-3}$ alkyl, =O, $C_{1-3}$ alkyl, $C_{1-3}$ alkoxy, and phenyl. Each substituent can independently be selected from deuterio, —OH, —NH$_2$, $C_{1-3}$ alkyl, and $C_{1-3}$ alkoxy.

"Sustained release" refers to release of a compound from a dosage form of a pharmaceutical composition at a rate effective to achieve a therapeutic or prophylactic concentration of the compound or active metabolite thereof, in the systemic circulation of a patient over a prolonged period of time relative to that achieved by administration of an immediate release formulation of the same compound by the same route of administration. In some embodiments, release of a compound occurs over a time period of at least about 4 hours, such as at least about 8 hours, at least about 12 hours, at least about 16 hours, at least about 20 hours, and in some embodiments, at least about 24 hours.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. "Treating" or "treatment" also refers to delaying the onset of the disease or delaying the onset of at least one or more symptoms thereof in a patient who may be exposed to or predisposed to a disease or disorder even though that patient does not yet experience or display symptoms of the disease.

"Therapeutically effective amount" refers to the amount of a compound that, when administered to a patient for treating a disease, or at least one of the clinical symptoms of a disease, is sufficient to affect such treatment of the disease or symptom thereof. A "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Vehicle" refers to a diluent, excipient or carrier with which a compound is administered to a patient. A vehicle can be a pharmaceutically acceptable vehicle. Pharmaceutically acceptable vehicles are known in the art.

"Binding affinity" refers to the strength of the binding interaction between a single biomolecule and its ligand/binding partner. Binding affinity is expressed as the IC$_{50}$ value. Binding affinity can be determined by phage ELISA competition assays.

"Modulate" and "modulation" refer to a change in biological activity for a biological molecule such as, for example, a protein, gene, peptide, or antibody, where such change may relate to an increase in biological activity such as, for example, increased activity, agonism, activation, expression, upregulation, and/or increased expression, or decrease in biological activity such as, for example, decreased activity, antagonism, suppression, deactivation, downregulation, and/or decreased expression, for the biological molecule.

For example, the compounds described herein can modulate such as inhibit p38α MAPK protein. Compounds provided by the preset disclosure can selectively modulate, such as selectively inhibit, p38α MAPK protein as compared to other MAPK or p38 MAPK proteins. Compounds provided by the present disclosure can selectively modulate such as selectively inhibit p38α MAPK protein as compared to other MAPK or p38 MAPK proteins.

"Moiety" refers to a specific segment or functional group of a molecule. Chemical moieties are often recognized chemical entities embedded in or appended to a molecule.

Reference is now made in detail to certain compounds, compositions, and methods. The disclosed compounds, compositions, and methods are not intended to be limiting of the claims. To the contrary, the claims are intended to cover all alternatives, modifications, and equivalents.

Compounds provided by the present disclosure are selective inhibitors of the p38α MAPK protein. Pharmaceutical compositions provided by the present disclosure include compounds provided by the present disclosure. Compounds and pharmaceutical compositions provided by the present disclosure can be used to treat diseases in which the disease is treated by inhibiting the p38α MAPK protein.

Catalytic inhibitors of p38α MAPK can block expression of proinflammatory cytokines and can block other p38α MAPK signaling pathways that are important for establishing and maintaining homeostasis.

As an alternative to the catalytic inhibitors, the compounds provided by the present disclosure target the substrate binding groove of p38α MAPK, which extends between two acidic patches, referred to as the CD and ED domains, of the MAPK receptor and is distinct from the DEF substrate-binding pocket. Downstream substrates, upstream activating kinases, and possibly scaffolding molecules, interact with p38 MAPK through these sites. Compounds provided by the present disclosure can selectively bind to p38α MAPK and not p38β, can stabilize endothelial barrier function in human lung microvascular endothelial cells (HMVE-CLs), and/or can inhibit lipopolysaccharide (LPS)-induced proinflammatory gene expression in THP-1 cells.

Compounds provided by the present disclosure include compounds of Formula (6) in which R$^2$ comprises a substituted fused ring, and compounds of Formula (6) in which R$^2$ comprises a substituted monocyclic ring. A compound provided by the present disclosure can have the structure of Formula (6):

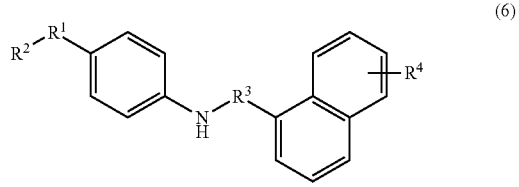

(6)

or a pharmaceutically acceptable salt thereof, wherein,

R$^1$ can be selected from C$_{1-4}$ alkanediyl, C$_{1-4}$ heteroalkanediyl, substituted C$_{1-4}$ alkanediyl, and substituted C$_{1-4}$ heteroalkanediyl;

R$^2$ can be substituted C$_{5-12}$ heterocycloalkyl;

R$^3$ can be selected from —C=O and —S(=O)$_2$; and

R$^4$ can be selected from —N(R$^5$)$_2$ wherein each R$^5$ can be independently selected from hydrogen and C$_{1-4}$ alkyl.

In a compound of Formula (6), each of the one or more substituents can be independently selected from, for example, —OH, =O, —NH$_2$, —NO$_2$, C$_{1-6}$ alkyl, C$_{1-6}$ alkoxy, C$_{1-6}$ cycloalkyl, C$_6$ aryl, C$_{1-6}$ heteroalkyl, C$_{1-6}$ heteroalkoxy, C$_{1-6}$ heterocycloalkyl, C$_{5-6}$ heteroaryl, substituted C$_{1-6}$ alkyl, substituted C$_{1-6}$ alkoxy, substituted C$_{1-6}$ cycloalkyl, substituted C$_6$ aryl, substituted C$_{1-6}$ heteroalkyl, C$_{1-6}$ substituted heteroalkoxy, substituted C$_{1-6}$ heterocycloalkyl, and substituted C$_{5-6}$ heteroaryl.

In a compound of Formula (6), each of the one or more substituents can be independently selected from —OH, =O, —NH$_2$, —NO$_2$, C$_{1-3}$ alkyl, C$_{1-3}$ alkoxy, C$_{1-3}$ heteroalkyl, C$_{1-3}$ heteroalkoxy, substituted C$_{1-3}$ alkyl, substituted C$_{1-3}$ alkoxy, substituted C$_{1-3}$ heteroalkyl, and substituted C$_{1-3}$ heteroalkoxy.

In a compound of Formula (6), each of the one or more substituents can be independently selected from, for example, —OH, =O, C$_{1-3}$ alkyl, and C$_{1-3}$ alkoxy.

In a compound of Formula (6), each of the one or more substituents can be =O.

In a compound of Formula (6), each of the one or more heteroatoms can independently be selected from N and O.

In a compound of Formula (6), R$^1$ can be C$_{1-4}$ alkanediyl.

In a compound of Formula (6), R$^1$ can be ethanediyl.

In a compound of Formula (6), R$^1$ can be methanediyl.

In a compound of Formula (6), R$^2$ can be substituted C$_6$ heterocycloalkyl.

In a compound of Formula (6), each of the one or more heteroatoms can be selected from O and N.

In a compound of Formula (6), R$^2$ can be 4-morpholinyl.

In a compound of Formula (6), R$^2$ can be substituted 4-morpholinyl.

In a compound of Formula (6), R$^2$ can be 3-substituted 4-morpholinyl.

In a compound of Formula (6), R$^2$ can be C$_5$ heterocycloalkyl, C$_6$ heterocycloalkyl, C$_7$ heterocycloalkyl, C$_8$ heterocycloalkyl, or C$_9$ heterocycloalkyl.

In a compound of Formula (6), R$^2$ can be bonded to R$^1$ through a nitrogen heteroatom of the C$_{5-12}$ heterocycloalkyl moiety.

In a compound of Formula (6), R$^2$ can be a monocyclic C$_{5-12}$ heteroalkyl ring in which a ring nitrogen heteroatom is bonded to R$^1$.

In a compound of Formula (6), R$^2$ can be a monocyclic C$_{5-12}$ heteroalkyl ring in which a ring nitrogen hetero atom is bonded to R$^1$ and having at least one ring oxygen heteroatom.

In a compound of Formula (6), R$^2$ can be a monocyclic C$_{5-12}$ heteroalkyl ring in which a ring nitrogen heteroatom is bonded to R$^1$ and having at least one ring oxygen heteroatom, and at least one oxo (=O) substituent.

In a compound of Formula (6), R$^2$ can be a bicyclic C$_{5-12}$ heteroalkyl ring in which a ring nitrogen heteroatom is bonded to R$^1$.

In a compound of Formula (6), R$^2$ can be a bicyclic C$_{5-12}$ heteroalkyl ring in which a ring nitrogen hetero atom is bonded to R$^1$ and having at least one ring oxygen heteroatom.

In a compound of Formula (6), R$^2$ can be a bicyclic C$_{5-12}$ heteroalkyl ring in which a ring nitrogen heteroatom is bonded to R$^1$ and having at least one ring oxygen heteroatom, and at least one oxo (=O) substituent.

In a compound of Formula (6), R$^2$ can be selected from 4λ$^2$-morpholin-3-one, 4λ$^2$-morpholin-2-one, 1,3λ$^2$-oxazinan-4-one, 1,3λ$^2$-oxazinan-5-one, 1,3λ$^2$-oxazinan-6-one, 3λ$^2$-oxazolidin-2-one, 3λ$^2$-oxazolidin-4-one, and 3λ$^2$-oxazolidin-5-one. [93] In a compound of Formula (6), each of the one or more substituents can be selected from —OH, =O, and —N(R$^5$)$_2$, wherein each R$^5$ can be independently selected from hydrogen and C$_{1-3}$ alkyl.

In a compound of Formula (6), each of the one or more substituents can be —OH.

In a compound of Formula (6), each of the one or more substituents can =O.

In a compound of Formula (6), each of the one or more substituents can be —N(R$^5$)$_2$, wherein each R$^5$ can be independently selected from hydrogen and C$_{1-3}$ alkyl.

In a compound of Formula (6), R$^3$ can be selected from C(=O) and S(O)$_2$.

In a compound of Formula (6), R$^3$ can be C(=O).

In a compound of Formula (6), R$^3$ can be S(O)$_2$.

In a compound of Formula (6), R$^4$ can be bonded to the 3-position, the 4-position, the 5-position, the 6-position, or the 7-position of the naphthyl moiety.

In a compound of Formula (6), R$^4$ can be bonded to the 5-position of the naphthyl moiety.

In a compound of Formula (6),
R$^1$ can be C$_{1-3}$ alkanediyl;
R$^2$ can be substituted 4-morpholinyl;
R$^3$ can be selected from C(=O) and S(O)$_2$; and
R$^4$ can be selected from —N(R$^5$)$_2$ wherein each R$^5$ can be independently selected from hydrogen and C$_{1-3}$ alkyl.

In a compound of Formula (6),
R$^1$ can be methane-diyl;
R$^2$ can be substituted 4-morpholinyl;
R$^3$ can be S(O)$_2$; and
R$^4$ can be —N(R$^5$)$_2$ wherein each R$^5$ can be independently selected from hydrogen and methyl.

In a compound of Formula (6),
R$^1$ can be methane-diyl;
R$^2$ can be substituted 4-morpholinyl;
R$^3$ can be C(=O); and
R$^4$ can be —N(R$^5$)$_2$ wherein each R$^5$ can be independently selected from hydrogen and methyl.

In a compound of Formula (6), R$^2$ can be 3-substituted 4-morpholinyl.

In a compound of Formula (6), in a moiety of R$^2$, the substituent can be =O.

In a compound of Formula (6), R$^4$ can be selected from —NH(—CH$_3$) and —N(—CH$_3$)$_2$.

In a compound of Formula (6), R$^4$ can be —NH(—CH$_3$).

In a compound of Formula (6), R$^4$ can be —N(—CH$_3$)$_2$.

A compound of Formula (6) can be selected from:
4-amino-N-(4-((3-oxomorpholino)methyl)phenyl)naphthalene-1-sulfonamide;
4-(methylamino)-N-(4-((3-oxomorpholino)methyl)phenyl)naphthalene-1-sulfonamide;
4-(dimethylamino)-N-(4-((3-oxomorpholino)methyl)phenyl)naphthalene-1-sulfonamide;
5-amino-N-(4-((3-oxomorpholino)methyl)phenyl)naphthalene-1-sulfonamide;
5-(methylamino)-N-(4-((3-oxomorpholino)methyl)phenyl)naphthalene-1-sulfonamide;
5-(dimethylamino)-N-(4-((3-oxomorpholino)methyl)phenyl)naphthalene-1-sulfonamide;
6-amino-N-(4-((3-oxomorpholino)methyl)phenyl)naphthalene-1-sulfonamide;
6-(methylamino)-N-(4-((3-oxomorpholino)methyl)phenyl)naphthalene-1-sulfonamide; and
6-(dimethylamino)-N-(4-((3-oxomorpholino)methyl)phenyl)naphthalene-1-sulfonamide;
or a pharmaceutically acceptable salt of any of the foregoing.

A compound of Formula (6) can be 5-amino-N-(4-((3-oxomorpholino)methyl)phenyl)naphthalene-1-sulfonamide (Compound 5), or a pharmaceutically acceptable salt thereof:

(5)

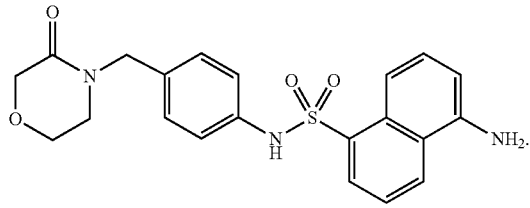 [SMILES: Nc1cccc2c(S(=O)(=O)Nc3ccc(CN4CCOCC4=O)cc3)cccc12]

A compound of Formula (6) can be 5-(methylamino)-N-(4-((3-oxomorpholino)methyl)phenyl)naphthalene-1-sulfonamide (2), or a pharmaceutically acceptable salt thereof:

(2)

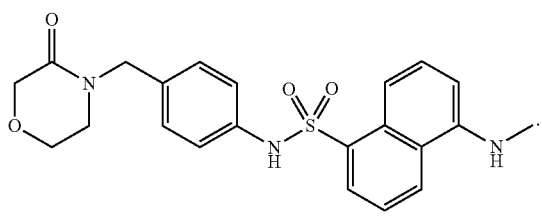 [SMILES: CNc1cccc2c(S(=O)(=O)Nc3ccc(CN4CCOCC4=O)cc3)cccc12]

A compound of Formula (6) can be 5-(dimethylamino)-N-(4-((3-oxomorpholino)methyl)phenyl)naphthalene-1-sulfonamide (3), or a pharmaceutically acceptable salt thereof:

(3)

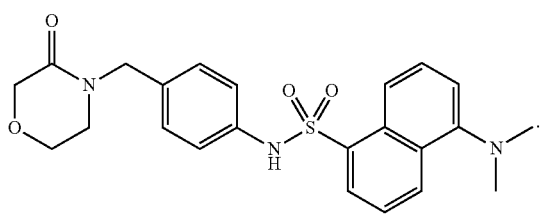

A compound of Formula (6) can be a solvate, a pharmaceutically acceptable salt, or a combination thereof.

In a compound of Formula (6), a pharmaceutically acceptable salt can be the hydrochloride salt.

A compound of Formula (6) can be a pharmaceutically acceptable salt of a compound of Formula (6), a hydrate thereof, or a solvate of any of the foregoing.

In certain embodiments, a compound provided by the present disclosure is not a compound of Formula (1) (5-(methylamino)-N-(4-(morpholinomethyl)phenyl)naphthalene-1-sulfonamide):

(1)

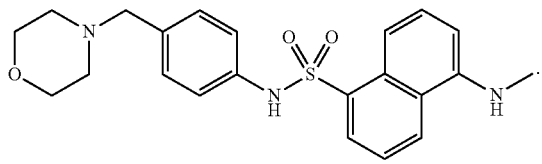

A compound provided by the present disclosure can be a p38 MAPK inhibitor such as a selective p38 MAPK inhibitor and/or a modulator of p38α MAPK protein activity.

A compound provided by the present disclosure can be a selective inhibitor of p38α MAPK. A selective p38α MAPK inhibitor provided by the present disclosure has a higher binding affinity (lower $IC_{50}$) to the target pocket of p38α MAPK than to the catalytic binding site of p38α MAPK. A compound provided by the present disclosure can selectively inhibit p38α MAPK. The p38α MAPK inhibitor can bind to p38α MAPK near the substrate binding groove of p38α MAPK, which extends between two acidic patches referred to as the CD and ED domains. The binding pocket can be defined at least by residues R49, H107, L108, and K165 of p38α MAPK. The binding pocket can be defined at least by residues R49, H107, L108, M109, G1 10, Al 57, V158, El 63, L164, and K165 of p38α MAPK. The binding pocket and method for determining selective binding to the selective binding pocket is described, for example, in U.S. Application No. 2020/0331874 A1 and in U.S. Application No. 2019/0151324 A1.

Selective binding of a compound provided by the present disclosure to p38α MAPK can be confirmed using complementary technologies. For example, a selective p38α MAPK inhibitor can show a concentration-dependent increase in melting temperature of p38α but not p38β as determined using differential scanning fluorimetry (DSF) to detect ligand-induced protein stabilization. STD-NMR, which measures low affinity protein/ligand binding via non-scalar magnetization transfer from protein to ligand protons, can be used to confirm specific compound binding to p38α and localize the interaction to the aromatic rings of the binding site. A p38α MAPK inhibitor can cause a concentration-dependent increase in melting temperature of p38α MAPK. The difference in melting temperature Tm can be measured at a p38α MAPK inhibitor concentration between 1 nM and 1,000 μM such as at a concentration of 100 μM. For example, the difference in the melting temperature can be from 0.1° C. to about 2° C.

A compound provided by the present disclosure can interact with a pocket near the ED substrate docking site of p38 MAPK.

A compound provided by the present disclosure can bind to p38α MAPK near the substrate binding groove of p38α MAPK, which extends between the CD and ED domains.

A compound provided by the present disclosure can inhibit MK2 phosphorylation through interaction with p38α MAPK.

A compound provided by the present disclosure can competitively bind to p38α MAPK with 4-chloro-N-(4-((1,1-dioxidothiomorpholino)methyl)phenyl)benzamide.

A compound provided by the present disclosure can have a higher binding affinity to the p38α MAPK subunit than to the p38β MAPK subunit.

A p38α MAPK inhibitor provided by the present disclosure can have a logP, for example, from −5 to 10, from −3 to 8, from 0 to 5, 0.1 to 3, from 0.1 to 1, from 0.5 to 1.5, from 0.75 to 2, from 1 to 2.5, or from 1.75 to 3. LogP is a measure of drug solubility and is defined as the logarithm of the octanol/water partition coefficient of the drug.

Phosphorylation of MK2 can involve binding to the ED site adjacent to the target pocket in p38α MAPK. The target pocket can be defined by amino acids R49, H107, L108, and K165 in p38α MAPK. The target pocket can be defined by amino acids selected from R49, H107, L108, M109, G1 10, Al 57, V158, El 63, L164, and K165 in p38α MAPK. The target pocket can be defined by the amino acids R49, H107, L108, M109, G1 10, Al 57, V158, El 63, L164, and K165 in p38α MAPK.

p38α MAPK inhibitors provided by the present disclosure can at least partially inhibit MK2 phosphorylation. For example, Western blotting can be used to measure inhibition of MK2 phosphorylation in anisomycin-stimulated HeLa cells by a compound provided by the present disclosure.

A p38α MAPK inhibitor provided by the present disclosure can stabilize an endothelial or epithelial barrier function. Endothelial barrier permeability can be measured by separate or combined exposure to TNFa and hyperthermia, followed by measurement of permeability for 10 kDa dextran. For example, endothelial barrier stabilization can be assessed by pretreating with a compound provided by the present disclosure, preceded and followed by permeability measurements, where stabilization can be expressed as a % reduction in the before and after pretreatment permeability increase. A permeability increase caused by 10 kDa dextran can be reduced by between 5% to more than 100% such as, for example, by greater than 5%, greater than 10%, greater than 20%, greeter than 40%, greater than 60%, greater than 80%, or greater than 100%.

A p38α MAPK inhibitor provided by the present disclosure can modulate TNFα-induced gene expression in human lung microvascular endothelial cells (HMVECLs) as determined using, for example, RNASeq. For example, HMVECLs can be pretreated for a period of time with a p38α MAPK inhibitor at an appropriate concentration and then stimulated with TNFa for a period of time. A p38α MAPK inhibitor provided by the present disclosure can inhibit genes such as PRRG4, TSLP, CCLI 7, EXOC3L4, MMP9, IDOI, CXCL1O, CD200, SLCI5A3, VDR, ILIB, GPR88, CD207, TCHH, HAS3, GBPIPI, MUC4, ELOVL7, CXCL11, GBP4, PLAIA, and/or CXCL5.

The effects of a p38α MAPK inhibitor on inflammatory cytokine expression can be determined by pretreating PMA-differentiated THPI cells with a p38α MAPK inhibitor, then stimulating with LPS, and harvesting RNA a period of time later for analysis by PCR-based cytokine array. A p38α MAPK inhibitor can inhibit expression of various genes, such as IL-IA, IL-8, TNFSF8, CXCL5, CCL7, CCLI 7, TNFSF9, IL-IB, CXCLI, TNFSFIS, CCL5, CCL4, CCL20, CXCL2, TNF, or BMP6. A p38α MAPK inhibitor can inhibit expression of Smad3, which drives differentiation of Foxp3 T regulatory cells and suppresses interferon-y. Inflammation reduction can be measured by comparing the fold change mRNA levels with unstimulated PMA-differentiated THPI cells at various concentrations of p38α MAPK inhibitor.

Certain compounds of Formula (6) can be metabolites of a corresponding compound N-(4-(morpholinomethyl)phenyl)naphthalene-1-sulfonamide having an amine substituent on the naphthyl moiety. For example, a compound of Formula (2) (5-(methylamino)-N-(4-((3-oxomorpholino)methyl)phenyl)naphthalene-1-sulfonamide; Compound 2) and a compound of Formula (3) (5-(dimethylamino)-N-(4-((3-oxomorpholino)methyl)phenyl)naphthalene-1-sulfonamide; Compound 3) can be metabolites of compound (4) (5-(dimethylamino)-N-(4-(morpholinomethyl)phenyl)naphthalene-1-sulfonamide; Compound (4)):

(2)

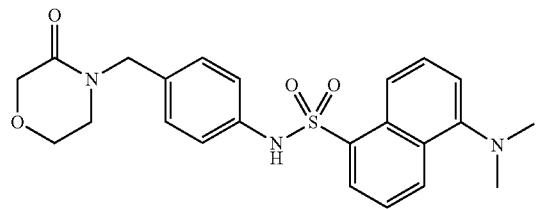

(3)

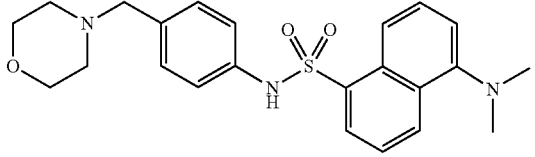 [SMILES: CN(C)c1cccc2c(S(=O)(=O)Nc3ccc(CN4CCOCC4)cc3)cccc12]

(4)

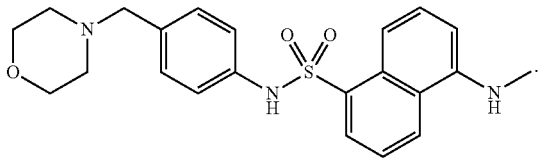

Following administration of compound (4) to a subject, compound (4) can be metabolized in vivo to provide a compound of Formula (3), a compound of Formula (2), and a compound of Formula (1) (5-(methylamino)-N-(4-(morpholinomethyl)phenyl)naphthalene-1-sulfonamide (Compound 1)):

(1)

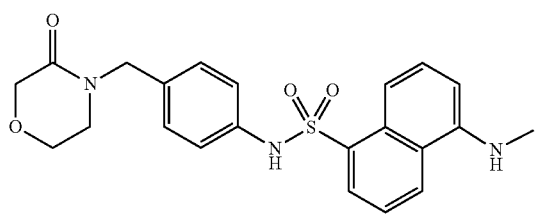

Compounds of Formula (6) can be synthesized using methods known in the art.

For example, (4-aminophenyl)methanol (A) can be reacted with Boc₂O in CH₂Cl₂ to provide the Boc-protected compound teat-butyl (4-(hydroxymethyl)phenyl)carbamate (B). The Boc-protected intermediate (B) can be reacted with PDC in CH₂Cl₂ to provide teat-butyl (4-acetylphenyl)carbamate (C). Intermediate (C) can be reacted with a suitable substituted morpholine in the presence of NaBH(OAc)₂ in an organic solvent such as 1,2-dichloroethane (DCE) to provide the corresponding substituted tent-butyl (4-(morpholinomethyl)phenyl)carbamate (D). Intermediate (D) can be deprotected in the presence of 4M HCl in methanol to provide the corresponding substituted 4-(morpholinomethyl)aniline dihydrochloride salt (E). The salt (E) can be reacted with a suitable substituted S-(naphthalen-1-yl) chlorothioate (F) in the presence of N,N-diisopropylethylamine (DIPEA) in dimethylformamide (DMF) to provide the corresponding compound of Formula (6).

Compounds provided by the present disclosure can be incorporated into pharmaceutical compositions to be administered to a patient by any appropriate route of administration including intradermal, intramuscular, intraperitoneal, intravenous, subcutaneous, intranasal, epidural, oral, peroral, sublingual, intracerebral, intravaginal, transdermal, rectal, inhalation, or topical. A pharmaceutical composition provided by the present disclosure can be an injectable formulation. A pharmaceutical composition provided by the present disclosure can be injectable intravenous formulation. A pharmaceutical composition provided by the present disclosure can be an oral formulation. An oral formulation can be an oral dosage form. A pharmaceutical composition can be formulated for intravenous administration or for subcutaneous administration.

A pharmaceutical composition provided by the present disclosure can comprise a therapeutically effective amount of a compound of Formula (6) together with a suitable amount of one or more pharmaceutically acceptable vehicles so as to provide a composition for proper administration to a patient. Suitable pharmaceutical vehicles and methods of preparing pharmaceutical compositions are described in the art.

Assessing single patient response to therapy and qualifying a patient for optimal therapy are among the greatest challenges of modern healthcare and motivate trends in personalized medicine. A compound of Formula (6) can have target selectivity, for example, for certain cancers and immune cells. A compound of Formula (6) radiolabeled for positron emission tomography (PET) or Single Photon Emission Computed Tomography (SPECT) can be used to predict the targeting of the treatment based on a single-study, case-by-case patient analysis thus excluding patients that are expected not to benefit from treatment. PET/SPECT scans using a compound of Formula (6), once correlated to the concentration can provide a three-dimensional distribution map, which can then be used for macroscopic dose calculations.

A compound of Formula (6) and/or pharmaceutical composition thereof can generally be used in an amount effective to achieve an intended purpose. For use to treat a disease such as cancer, an autoimmune disease or an inflammatory disease, a compound of Formula (6) and/or pharmaceutical composition thereof, may be administered or applied in a therapeutically effective amount.

The amount of a compound of Formula (6) and/or pharmaceutical composition of any of the foregoing that will be effective in the treatment of a particular disorder or condition will depend in part on the nature of the disorder or condition, and can be determined by standard clinical techniques known in the art. In addition, in vitro or in vivo assays may optionally be employed to help identify optimal dosage ranges. The amount of a compound of Formula (6), and/or pharmaceutical composition of any of the foregoing administered will depend on, among other factors, the patient being treated, the weight of the patient, the severity of the affliction, the manner of administration and the judgment of the prescribing physician.

A compound of Formula (6) can be assayed in vitro and in vivo, for the desired therapeutic activity, prior to use in humans. For example, in vitro assays may be used to determine whether administration of a specific compound or a combination of compounds is preferred. The compounds can also be demonstrated to be effective and safe using animal model systems.

In certain embodiments, a therapeutically effective dose of a compound of Formula (6) and/or pharmaceutical composition of any of the foregoing will provide therapeutic benefit without causing substantial toxicity. Toxicity of a compound of Formula (6) and/or pharmaceutical compositions of any of the foregoing may be determined using standard pharmaceutical procedures and may be readily ascertained by the skilled artisan. The dose ratio between toxic and therapeutic effect is the therapeutic index. A compound of Formula (6) and/or pharmaceutical composition of any of the foregoing exhibits a particularly high therapeutic index in treating disease and disorders. A dose of a compound of Formula (6) compound, and/or pharmaceutical composition of any of the foregoing will be within a range of circulating concentrations that include an effective dose with minimal toxicity.

Compounds and pharmaceutical compositions provided by the present disclosure can be included in a kit that can be used to administer the compound to a patient for therapeutic purposes. A kit can include a pharmaceutical composition comprising a compound provided by the present disclosure suitable for administration to a patient and instructions for administering the pharmaceutical composition to the patient. The kit can be suitable for treating cancer, for treating an autoimmune disease, or for treating an inflammatory disease. A kit for use in treating cancer, for treating an autoimmune disease, or for treating an inflammatory disease can comprise a compound or a pharmaceutical composition provided by the present disclosure, and instructions for administering the compound to a patient.

Compounds and pharmaceutical compositions provided by the present disclosure can be included in a container, pack, or dispenser together with instructions for administration.

Instructions supplied with a kit may be printed and/or supplied, for example, as an electronic-readable medium, a video cassette, an audiotape, a flash memory device, or may be published on an internet web site or distributed to a patient and/or health care provider as an electronic communication.

Compounds and pharmaceutical compositions provided by the present disclosure can be used to treat a disease in a patient.

Compounds and pharmaceutical compositions provided by the present disclosure can be used to treat a disease in which the etiology of the disease is associated with up-regulation and/or down-regulation of the p38α MAPK protein.

Methods provided by the present disclosure include treating a disease in a patient comprising administering to a patient in need of such treatment a therapeutically effective amount of a compound or composition provided by the present disclosure, wherein the disease is treated by inhibiting the p38α MAPK protein.

The p38 mitogen-activated protein kinase (MAPK) family of stress- and cytokine-activated kinases are associated with the pathogenesis of many human diseases, including, for example, cancer, rheumatoid arthritis, cardiovascular disease, multiple sclerosis, inflammatory bowel disease, chronic obstructive pulmonary disease (COPD), asthma, acute respiratory distress syndrome (ARDS), and acute lung injury (ALI). Among the many important biological processes regulated by p38 MAPK, regulation of endothelial and epithelial barrier function, leukocyte trafficking, and cytokine expression are central to the pathogenesis of acute and chronic inflammatory disorders.

Compounds and pharmaceutical compositions provided by the present disclosure may be used for treating cancer in a patient. The cancer can be, for example, a solid tumor or a metastasis.

Methods provided by the present disclosure include methods of treating cancer in a patient comprising administering to a patient in need thereof a therapeutically effective amount of a compound or pharmaceutical composition provided by the present disclosure.

Examples of suitable cancers include acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rhabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular carcinoma, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, and Hodgkin's disease.

Examples of suitable cancers include pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, or retinoblastoma. A cancer can be acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rhabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilms tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, multiple myeloma, non-Hodgkin's lymphoma, polycythemia vera, or Waldenstrom macroglobulinemia.

Compounds and pharmaceutical compositions provided by the present disclosure can be used to treat, for example, one or more of the following cancers: acute lymphoblastic leukemia, acute myeloid leukemia, adrenocortical carcinoma, appendix cancer, astrocytoma, atypical teratoid/rhabdoid tumor, basal cell carcinoma (nonmelanoma), B-cell lymphoma, bladder cancer, bone cancer, brain and spinal cord tumors, brain stem cancer, brain tumor, breast cancer, bronchial tumors, Burkitt lymphoma, carcinoid tumor, carcinoma of head and neck, central nervous system embryonal tumors, cerebellar astrocytoma, cerebral astrocytoma/malignant glioma, cervical cancer, chordoma, chronic lymphocytic leukemia, chronic myelogenous leukemia, colorectal cancer, craniopharyngioma, cutaneous T-cell lymphoma, desmoplastic small round cell tumor, ductal carcinoma, dye cancer, endocrine pancreas tumors (islet cell tumors), endometrial cancer, ependymoblastoma, esophageal cancer, esthesioneuroblastoma, Ewing family of tumors, extracranial germ cell tumor, extrahepatic bile duct cancer, gallbladder cancer, gastric cancer, gastrointestinal carcinoid tumor, gastrointestinal stromal tumor, gestational trophoblastic tumor, glioblastoma, glioma, hairy cell leukemia, head and neck cancer, heart cancer, hematopoetic tumors of the lymphoid lineage, hepatocellular cancer, Hodgkin lymphoma, hypopharyngeal cancer, hypothalamic and visual pathway glioma, IDs-related lymphoma, intraocular melanoma, islet cell tumors, Kaposi sarcoma, kidney cancer, Langerhans cell histiocytosis, laryngeal cancer, leukemia, lip and oral cavity cancer, male breast cancer, malignant fibrous histiocytoma, malignant germ cell tumors, malignant mesothelioma, medulloblastoma, melanoma, Merkel cell carcinoma, mesothelioma, mouth cancer, multiple endocrine neoplasia syndrome, multiple myeloma, mycosis fungoides, myelodysplastic, myeloproliferative neoplasms, nasal cavity and paranasal sinus cancer, nasopharyngeal cancer, neuroblastoma, non-Hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, primary liver cancer, primary metastatic squamous neck cancer with occult, prostate cancer, rectal cancer, renal cell cancer, renal pelvis and ureter, respiratory tract carcinoma, retinoblastoma, rhabdomyosarcoma, salivary gland cancer, sarcoma, Sézary syndrome, skin cancer, small intestine cancer, soft tissue sarcoma, squamous cell carcinoma (nonmelanoma), stomach cancer, supratentorial primitive neuroectodermal tumors, T-cell lymphoma, testicular cancer, throat cancer, thymoma and thymic carcinoma, thyroid cancer, transitional cell cancer, urethral cancer, uterine sarcoma, vaginal cancer, visual pathway and hypothalamic glioma, vulvar cancer, Waldenström macroglobulinemia, Wilms tumor, and systemic and central metastases of any of the foregoing.

Methods provided by the present disclosure include methods of treating cancer, where the cancer is selected from breast cancer and melanoma.

Methods provided by the present disclosure include methods of treating an inflammatory disease in a patient comprising administering to a patient in need thereof a therapeutically effective amount of a compound or pharmaceutical composition provided by the present disclosure.

Examples of inflammatory diseases include allergy, Alzheimer's disease, anemia, ankylosing spondylitis, arthritis, atherosclerosis, asthma, autism, arthritis, carpal tunnel syndrome, celiac disease, colitis, Crohn's disease, congestive heart failure, dermatitis, diabetes, diverticulitis, eczema, fibromyalgia, fibrosis, gall bladder disease gastroesophageal reflux disease, Hashimoto's thyroiditis, heart attack, hepatitis, irritable bowel syndrome, kidney failure, lupus, multiple sclerosis, nephritis, neuropathy, pancreatitis, Parkinson's disease, psoriasis, polymyalgia rheumatica, rheumatoid arthritis, scleroderma, stroke, surgical complications, and ulcerative colitis.

Methods provided by the present disclosure include methods of treating an inflammatory disease in a patient, where the inflammatory disease is selected from, for example, acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes including Type 1 diabetes and Type 2 diabetes, and rheumatoid arthritis.

Methods provided by the present disclosure include methods of treating an autoimmune disease in a patient comprising administering to a patient in need thereof a therapeutically effective amount of a compound or pharmaceutical composition provided by the present disclosure.

A compound or a pharmaceutical composition provided by the present disclosure can be useful in treating autoimmune diseases. Autoimmune diseases can be defined as human diseases in which the immune system attacks its own proteins, cells, and/or tissues. A comprehensive listing and review of autoimmune diseases can be found, for example, in *The Autoimmune Diseases*, Rose and Mackay, 2014, Academic Press.

Examples of autoimmune diseases include Addison's disease, agammaglobulinemia, alopecia areata, amyloidosis, ankylosing spondylitis, anti-GBM/anti-TBN nephritis, antiphospholipid syndrome, autoimmune angioedema, autoimmune dysautonomia, autoimmune encephalomyelitis, autoimmune hepatitis, autoimmune inner ear disease, autoimmune myocarditis, autoimmune pancreatitis, autoimmune retinopathy, autoimmune urticaria, axonal and neuronal neuropathy, Balo disease, Bechet's disease, benign mucosal pemphigoid, bullous pemphigoid, Castleman disease, celiac disease, Chagas disease, chronic inflammatory demyelinating polyneuropathy, chronic recurrent multifocal osteomyelitis, Churg-Strauss, cicatricial pemphigoid, Cogan' syndrome, cold agglutinin disease, congenital heart block, Coxcackie myocarditis, CREST syndrome, Crohn's disease, dermatitis herpetiformis, dermatomyositis, Devic's disease, discoid lupus, Dressler's syndrome, endometriosis, eosinophilic esophagitis, eosinophilic fasciitis, erythema nodosum, essential mixed cryoglobulinemia, Evans syndrome, fibromyalgia, fibrosing alveolitis, giant cell arteritis, giant cell myocarditis, glomerulonephritis, Goodpasture's syndrome, granulomatosis with polyangiitis, Graves' disease, Gullain-Barre syndrome, Hashimoto's thyroiditis, hemolytic anemia, Henoch-Schoenlein purpura, herpes gestationis or pemphigoid gestationis, hypogammaglobulinemia, IgA nephropathy, IgG4-related sclerosing disease, immune thrombocytopenic purpura, inclusion body myositis, interstitial cystitis, juvenile arthritis, juvenile diabetes, juvenile myositis, Kawasaki disease, Lambert-Eaton syndrome, leukocytoclastic vasculitis, lichen planus, lichen sclerosis, ligneous conjunctivitis, linear IgA disease, lupus, Lyme disease chronic, Meniere's diseases, microscopic polyangiitis, mixed connective tissue disease, Mooren's ulcer, Mucha Habermann disease, multiple sclerosis, myasthenia gravis, myositis, narcolepsy, neuromyelitis, optica, neutropenia, ocular cicatricial pemphigoid, optic neuritis, palindromic rheumatism, PANDAS, paraneoplastic cerebellar degeneration, paroxysmal nocturnal hemoglobinuria, Parry Romberg syndrome, pars planitis, Parsonnage-Turner syndrome, pemphigus, peripheral neuropathy, perivenous encephalomyelitis, pernicious anemia, POEMS syndrome, polyarteritis nodosa, polyglandular syndromes, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic ophthalmia, Takayasu's arteritis, temporal arteritis, thrombocytopenic purpura, Tolosa-Hunt syndrome, transverse myelitis, type 1 diabetes, ulcerative colitis, undifferentiated connective tissue disease, uveitis, vaculitis, vitiligo, and Wegener's granulomatosis.

A compound or a pharmaceutical composition provided by the present disclosure can be used to treat autoimmune disorders such as, for example, lupus, graft-versus-host disease, hepatitis C-induced vasculitis, Type I diabetes, multiple sclerosis, spontaneous loss of pregnancy, an atopic disease, and an inflammatory bowel disease.

A compound or a pharmaceutical composition provided by the present disclosure can be administered with one or more additional therapeutic agents for treating an autoimmune disease. A compound of Formula (6) or a pharmaceutical composition thereof may be administered in conjunction with one or more immunosuppressants including, for example, corticosteroids such as prednisone, budesonide, and prednisolone; Janus kinase inhibitors such as tofacitinib; calcineurin inhibitors such as cyclosporine and tacrolimus; mTOR inhibitors such as sirolimus and everolimus; IMDH inhibitors such as azathioprine, leflunomide, and mycophenolate; biologics such as abatacept adalimumab, anakinra, certolizumab, etanercept, golimumab, infliximab, ixekizumab, natalizumab, rituximab, secukinumab, tocilizumab, ustekinumab, and vedolizumab; and monoclonal antibodies such as basiliximab and daclizumab.

Methods provided by the present disclosure include methods of treating a disease in a patient comprising administering to a patient in need thereof a therapeutically effective amount of a compound or pharmaceutical composition provided by the present disclosure, wherein the disease is selected from acute coronary syndrome, acute lung injury, acute respiratory distress syndrome (ARDS), Alzheimer's disease, asthma, a cardiovascular disease, chronic obstructive pulmonary disease (COPD), inflammatory bowel disease, major depressive disorder, multiple sclerosis, neuropathic pain, and rheumatoid arthritis.

A compound or a pharmaceutical composition provided by the present disclosure can be administered with one or more additional therapeutic agents for treating an age-related disease such as hearing loss, muscle regeneration, and Werner's syndrome.

Methods provided by the present disclosure include methods of treating a disease in a patient comprising administering to a patient in need thereof a therapeutically effective amount of a compound or pharmaceutical composition provided by the present disclosure, wherein the disease is an age-related disease such as, for example, hearing loss, muscle degeneration, Werner's syndrome, cellular aging, or Alzheimer's disease.

Methods provided by the present disclosure include methods of treating a disease in a patient comprising administering to a patient in need thereof a therapeutically effective amount of a compound or pharmaceutical composition provided by the present disclosure, wherein the disease is selected from sudden idiopathic hearing loss, drug induced hearing loss, age-related hearing loss, and Duchenne muscular dystrophy.

Methods provided by the present disclosure include methods of treating a viral disease in a patient comprising administering to a patient in need thereof a therapeutically effective amount of a compound or pharmaceutical composition provided by the present disclosure. A viral disease can be SARS-CoV-19 and SARS-CoV-2.

The amount of a compound of Formula (6) provided by the present disclosure, or pharmaceutical composition thereof that will be effective in the treatment of a disease can depend, at least in part, on the nature of the disease, and may be determined by standard clinical techniques known in the art. In addition, in vitro or in vivo assays may be employed to help identify optimal dosing ranges. Dosing regimens and dosing intervals may also be determined by methods known to those skilled in the art. The amount of a compound of Formula (6) provided by the present disclosure administered may depend on, among other factors, the patient being treated, the weight of the patient, the severity of the disease, the route of administration, and the judgment of the prescribing physician.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of a compound of Formula (6) provided by the present disclosure and appropriate dosing intervals may be selected to maintain a sustained therapeutically effective concentration of a compound of Formula (6) provided by the present disclosure in the blood of a patient, and in certain embodiments, without exceeding a minimum adverse concentration.

A pharmaceutical composition comprising a compound of Formula (6) provided by the present disclosure may be administered, for example once per week, every 2 weeks, every 3 weeks, every 4 weeks, every 5 weeks, or every 6 weeks. Dosing may be provided alone or in combination with other drugs and may continue as long as required for effective treatment of the disease. Dosing may also be undertaken using continuous or semi-continuous administration over a period of time. Dosing includes administering a pharmaceutical composition to a mammal, such as a human, in a fed or fasted state.

A pharmaceutical composition may be administered in a single dosage form or in multiple dosage forms or as a continuous or an accumulated dose over a period of time. When multiple dosage forms are used the amount of a compound of Formula (6) provided by the present disclosure contained within each of the multiple dosage forms may be the same or different.

Suitable daily dosage ranges for administration can range, for example, from about 2 µg to about 200 mg of a compound of Formula (6) provided by the present disclosure per kilogram body weight.

Suitable daily dosage ranges for administration may range, for example, from about 1 µg to about 50 mg of a compound of Formula (6) provided by the present disclosure per square meter ($m^2$) of body surface.

A compound of Formula (6) provided by the present disclosure may be administered to treat cancer in a patient in an amount, for example, from 0.001 mg/day to 100 mg/day, or in any other appropriate daily dose. A dose can be, for example, from 0.01 µg/kg body weight/week to 100 µg/kg body weight/week or any other suitable dose.

A pharmaceutical composition comprising a compound of Formula (6) provided by the present disclosure may be administered to treat cancer in a patient so as to provide a therapeutically effective concentration of a compound of Formula (6) provided by the present disclosure in the blood or plasma of the patient. A therapeutically effective concentration of a compound of a compound of Formula (6) provided by the present disclosure in the blood of a patient can be, for example, from 0.01 µg/L to 1,000 µg/L, from 0.1 µg/L to 500 µg/L, from 1 µg/L to 250 µg/L, or from about 10 µg/L to about 100 µg/L. A therapeutically effective concentration of a compound of Formula (6) provided by the present disclosure in the blood of a patient can be, for example, at least 0.01 µg/L, at least 0.1 µg/L, at least 1 µg/L, at least about 10 µg/L, or at least 100 µg/L. A therapeutically effective concentration of a compound of Formula (6) in the blood of a patient can be, for example, less than an amount that causes unacceptable adverse effects including adverse effects to homeostasis. A therapeutically effective concentration of a compound of Formula (6) in the blood of a patient can be an amount sufficient to restore and/or maintain homeostasis in the patient.

Pharmaceutical compositions provided by the present disclosure may be administered to treat a disease in a patient so as to provide a therapeutically effective concentration of a compound of Formula (6) in the blood of a patient for a period of time such as, for example, for 4 hours, 8 hours, 12 hours, 16 hours, 20 hours, 1 day, or 2 days.

The amount of a compound of Formula (6) administered may vary during a treatment regimen.

Pharmaceutical compositions provided by the present disclosure may further comprise one or more pharmaceutically active compounds in addition to a compound of Formula (6). Such compounds may be provided, for example, to treat the cancer being treated with the compound of Formula (6) or to treat a disease, disorder, or condition other than the cancer being treated with the compound of Formula (6), to treat a side-effect caused by administering the compound of Formula (6), to augment the efficacy of the compound of Formula (6), and/or to modulate the activity of the compound of Formula (6).

A compound of Formula (6) provided by the present disclosure may be administered in combination with at least one other therapeutic agent. A compound of Formula (6) may be administered to a patient together with another compound for treating cancer in the patient. The at least one other therapeutic agent can be a second, different compound of Formula (6). A compound of Formula (6) and the at least one other therapeutic agent may act additively or, and in certain embodiments, synergistically with another compound of Formula (6). The at least one additional therapeutic agent may be included in the same pharmaceutical composition or vehicle comprising the compound of Formula (6) or may be in a separate pharmaceutical composition or vehicle. Accordingly, methods provided by the present disclosure further include, in addition to administering a compound of Formula (6), administering one or more therapeutic agents effective for treating cancer or a different disease, disorder or condition than cancer. Methods provided by the present disclosure include administration of a compound of Formula (6) and one or more other therapeutic agents provided that the combined administration does not inhibit the therapeutic efficacy of the compound of Formula (6) and/or does not produce adverse combination effects.

A pharmaceutical composition comprising a compound of Formula (6) may be administered concurrently with the administration of another therapeutic agent, which may be part of the same pharmaceutical composition as, or in a different pharmaceutical composition than that comprising a compound of Formula (6). A compound of Formula (6) may be administered prior or subsequent to administration of another therapeutic agent. In certain combination therapies, the combination therapy may comprise alternating between administering a compound of Formula (6) and a composition comprising another therapeutic agent, e.g., to minimize adverse drug effects associated with a particular drug. When a compound of Formula (6) is administered concurrently with another therapeutic agent that potentially may produce an adverse drug effect including, for example, toxicity, the other therapeutic agent may be administered at a dose that falls below the threshold at which the adverse drug reaction is elicited.

A pharmaceutical composition comprising a compound of Formula (6) provided by the present disclosure may be administered with one or more substances, for example, to enhance, modulate and/or control release, bioavailability, therapeutic efficacy, therapeutic potency, and/or stability, of the compound of Formula (6). For example, a pharmaceutical composition comprising a compound of Formula (6) can be co-administered with an active agent having pharmacological effects that enhance the therapeutic efficacy of the compound of Formula (6).

A compound of Formula (6), or a pharmaceutical composition thereof may be administered in conjunction with an agent known or believed to be effective in treating a disease such as cancer, an autoimmune disease or an inflammatory disease in a patient, such as the same disease being treated with the compound of Formula (6).

A compound of Formula (6), or a pharmaceutical composition thereof may be administered in conjunction with an agent known or believed to interfere with cell proliferation.

A compound of Formula (6), or a pharmaceutical composition thereof may be administered in conjunction with an agent known or believed to interfere with cellular metabolism, to be an anti-metabolite, to interfere with RNA transcription, to interfere with RNA translation, to interfere with cellular protein synthesis, to interfere with synthesis of precursors for DNA synthesis and replication, to interfere with purine synthesis, to interfere with nucleoside synthesis, to interact with mTOR, to be an mTOR inhibitor, to interfere with cell cycle checkpoints.

A compound of Formula (6) or a pharmaceutical composition thereof may be administered in conjunction with a checkpoint inhibitor including a CTLA-4 inhibitor such as ipilimumab, a PD-1 inhibitor such as pembrolizumab and nivolumab, and/or a PD-LI inhibitor such as atezolizumab, avelumab, and durvalumab. A compound of Formula (6) or a pharmaceutical composition thereof may be administered in conjunction with an immunomodulator such as CD137/ 4-1BB, CD27, GIYR, and/or OC40.

A compound of Formula (6) or a pharmaceutical composition thereof may be administered in conjunction with an agent known or believed to be cytotoxic, to cause DNA damage, to cause cell cycle arrest, or to cause mitotic catastrophe.

A compound of Formula (6) or a pharmaceutical composition thereof may be administered in conjunction with an agent known or believed to modulate glutathione concentration, to modulate glutathione concentration within cells, to decrease glutathione concentration within cells, to reduce glutathione uptake into cells, to reduce glutathione synthesis, or to reduce glutathione synthesis within cells.

A compound of Formula (6) or a pharmaceutical composition thereof may be administered in conjunction with an agent known or believed to interfere with neovascularization, to reduce neovascularization, or to promote neovascularization.

A compound of Formula (6) or a pharmaceutical composition thereof may be administered in conjunction with an agent known or believed to interfere with hormone homeostasis, to interfere with hormone synthesis, to interfere with hormone receptor binding, or to interfere with hormone signal transduction.

A compound of Formula (6) or a pharmaceutical composition thereof may be administered in conjunction with an agent known or believed to interfere with growth factor homeostasis, to interfere with growth factor receptor expression, to interfere with growth factor binding to growth factor receptors, to interfere with growth factor receptor signal transduction, to interfere with the Hedgehog (Hh) signaling, to inhibit the Hedgehog pathway signaling, to inhibit ALK (anaplastic lymphoma kinase) pathway signaling, or to inhibit the non-homologous end joining (NHEJ) pathway.

A compound of Formula (6) or a pharmaceutical composition thereof may be administered in conjunction with one or more agents known or believed to be a VEGFR (vascular endothelial growth factor receptor) inhibitor, a RTK (receptor tyrosine kinase) inhibitor, a sodium channel current blocker, aFAK (focal adhesion kinase) inhibitor, a GLI (glioma-associated oncogene) inhibitor, a GLI1 inhibitor, a GLI2 inhibitor, a GLI3 inhibitor, a MAPK (mitogen-activated protein kinase) inhibitor, a MAPK/ERK pathway (also known as Ras-Raf-MEK-ERK pathways) inhibitor, a MEK1 inhibitor, a MEK2 inhibitor, a MEK5 inhibitor, a MEK5/ ERK5 inhibitor, aRTA (renal tubular acidosis) inhibitor, a ALK (anaplastic lymphoma kinase) inhibitor, Aa LK kinase inhibitor, a nuclear translocation inhibitor, a PORCN (porcupine) inhibitor, a 5-ARI (5α-reductase inhibitor), topoisomerase inhibitor, a Ras (rat sarcoma) inhibitor, a K-ras inhibitor, a CERK (ceramide kinase) inhibitor, a PKB (protein kinase B, also known as AKT) inhibitor, a AKT1 inhibitor, EZH2 (enhancer of zeste homolog 2) inhibitor, a BET (bromodomain and extraterminal domain motif) inhibitor, a SYK (spleen tyrosine kinase) inhibitor, JAK (Janus kinase) inhibitors, a SYK/JAK inhibitor, a IDO (indoleamine-pyrrole 2,3-dioxygenase) inhibitor, a IDO1 inhibitor, a RXR (retinoic X receptors) activating agent, a selective RXR activating agent, a p-glycoprotein inhibitor, a ERK inhibitor, a PI3K (phosphatidylinositol-4,5-bisphosphate 3-kinase) inhibitor, a BRD (bromodomain-containing protein) inhibitor, a BRD2 inhibitor, a BRD3 inhibitor, a BRD4 inhibitor, a BRDT (bromodomain testis-specific protein) inhibitor, a reverse transcriptase inhibitor, a NRT (nucleoside analog reverse-transcriptase) inhibitor, a PIM (proviral integrations of Moloney virus) inhibitor, a EGFR (epidermal growth factor receptor) inhibitor, a photosensitizer, a radiosensitizer, a ROS (proto-oncogene, receptor tyrosine kinase) inhibitor, a ROS1 (proto-oncogene 1) inhibitor, a CK (casein kinase) inhibitor, a CK2 inhibitor, a Bcr-Abl (breakpoint cluster region-Abelson proto-oncogene) tyrosine-kinase inhibitor such as dasatinib, a microtubule stabilizing agent, a microtubule depolymerization/disassembly inhibitor, a DNA intercalator, an androgen receptor antagonist, a chemoprotective agents, a HDAC (histone deacetylase) inhibitor, a DPP (dipeptidyl peptidase) inhibitor, a DPP-4 inhibitor, BTK (Bruton's tyrosine kinase) inhibitor, a kinase inhibitor such as imatinib, a tyrosine kinase inhibitor such as nilotinib, a ARP (poly (ADP-ribose) polymerase) inhibitor, a CDK (cyclin-dependent kinase) inhibitor, a CDK4 inhibitor, a CDK6 inhibitor, a CDK4/6 inhibitor, a HIF1α (hypoxia-inducible factor 1-α) inhibitor, a DNA ligase inhibitor, a DNA ligase IV inhibitor, a NHEJ (non-homologous end joining) inhibitor, a DNA ligase IV, a NHEJ inhibitor and a RAF inhibitor, a TKI and a RAF inhibitor, a TKI and RAF inhibitor such as sorafenib, a PDT (photodynamic therapy) sensitizer, an ATR (ataxia telangiectasia- and Rad3-related protein kinase) inhibitor, or a combination of any of the foregoing.

A compound of Formula (6) or a pharmaceutical composition thereof may be administered in conjunction with one or more chemotherapeutic agents, such as, for example, a VEGFR inhibitor such as fruquintinib, motesanib/AMG-706, vatalanib; a RTK inhibitor such as ponatinib; a sodium channel blocker such as GS967; a FAK inhibitor such as TAE226; a GLI1 and GLI2 inhibitor such as GANT61, a MEK inhibitor such as binimetinib; a RTA inhibitor such as linifanib; an ALK inhibitor such as brigstinib; bromopyruvic acid; a DNA alkylating agent such as thiotepa; nuclear translocations factors such as JSH-23; a PORCn inhibitor such as Wnt-059; a 5α-reductase inhibitor such as dutasteride; a topoisomerase inhibitor such as carubicin; a RAS inhibitor such as Kobe0065; a CerK inhibitor such as NVP-231; an AKT inhibitor such as uprosertib; a EZH2 inhibitor such as GSK-503; a BET bromodomain inhibitor such as OTX015; a MEKS/ERKS inhibitor such as BIX02189; a Syl/JAK inhibitor such as cerdulatinib; an IDO1 inhibitor such as NLG919; a retinoic X receptor activating agent such as bexsrotene; a PGP inhibitor such as acotiamide or actotiamide HCl; an Erk inhibitor such SCH772984; a PI3K inhibitor such as gedatolisib; a JAK inhibitor such as ruxolitinib; an AKT inhibitor such as afuresertib or afuresertib HCl; an ALK1 inhibitor such as ceritinib; an HDAC inhibitor such as abexinostat; a DPP inhibitor such as oamarigliptin; an EGFR inhibitor such as gefittinib; an EZH2 inhibitor such as GSK126; a BTK inhibitor such as ibrutinib; a kinase inhibitor such as imatinin HCl; an IDO inhibitor such as INCB024360; a DNA crosslinker such as mitomycin C; a tyrosine kinase inhibitor such as nilotinib, a PARP inhibitor such as olaparib; a tubulin stabilization promoter such as paclitaxel; a CDK4/6 inhibitor such as palbociclib; a RTK inhibitor such as sunitinib; a PDT sensitizer such as tslsporfin; a p-glycoprotein inhibitor such as tariquidar; an ATR inhibitor such as VE-822; an HDAC inhibitor such as PCI-24781; a DPP inhibitor such as omarigliptin; an EGFR inhibitor such as gefinib; an EZH2 inhibitor such as GSK126; a BTK inhibitor such as irbrutinib; an IDO inhibitor such as INCB024360; or a combination of any of the foregoing.

A compound of Formula (6) or a pharmaceutical composition thereof may be administered in conjunction with another chemotherapeutic agent, such as, for example, N-acetyl cysteine (NAC), adriamycin, alemtuzumab, amifostine, arsenic trioxide, ascorbic acid, bendamustine, bevacizumab, bortezomib, busulfan, buthionine sulfoxime, carfilzomib, carmustine, clofarabine, cyclophosphamide, cyclosporine, cytarabine, dasatinib, datinomycin, defibrotide, dexamethasone, docetaxel, doxorubicin, etoposide, filgrastim, floxuridine, fludarabine, gemcitabine, interferon alpha, ipilimumab, lenalidomide, leucovorin, melphalan, mycofenolate mofetil, paclitaxel, palifermin, panobinostat, pegfilrastim, prednisolone, prednisone, revlimid, rituximab, sirolimus, sodium 2-mercaptoethane sulfonate (MESNA), sodium thiosulfate, tacrolimus, temozolomide, thalidomide, thioguanine, thiotepa, topotecan, velcade, or a combination of any of the foregoing.

A compound of Formula (6) or a pharmaceutical compositions thereof can be used in combination therapy with other chemotherapeutic agents including one or more antimetabolites such as folic acid analogs; pyrimidine analogs such as fluorouracil, floxuridine, and cytosine arabinoside; purine analogs such as mercaptopurine, thiogunaine, and pentostatin; natural products such as vinblastine, vincristine, etoposide, tertiposide, dactinomycin, daunorubicin, doxorubicin, bleomycin, mithamycin, mitomycin C, L-asparaginase, and interferon alpha; platinum coordination complexes such as cis-platinum, and carboplatin; mitoxantrone; hydroxyurea; procarbazine; hormones and antagonists such as prednisone, hydroxyprogesterone caproate, medroxyprogesterone acetate, megestrol acetate, diethylstilbestrol, ethinyl estradiol, tamoxifen, testosterone propionate, fluoxymesterone, flutamide, and leuprolide, anti-angiogenesis agents or inhibitors such as angiostatin, retinoic acids, paclitaxel, estradiol derivatives, and thiazolopyrimidine derivatives; apoptosis prevention agents; triptolide; colchicine; luliconazole; and radiation therapy.

A compound of Formula (6) or a pharmaceutical composition thereof may be co-administered with a compound that inhibits DNA repair such as, for example, O6-benzylguanine (O6-BG).

A compound of Formula (6) or a pharmaceutical composition thereof may be administered in conjunction with one or more chemotherapeutic agents, such as, for example, abarelix, abiraterone, abiraterone acetate, n-acetyl cysteine, aclarubicin hydrochloride, adriamycin, adenine, afatinib, afatinib dimaleate, alemtuzumab, alendronate sodium, alitretinoin, allopurinol sodium, altretamine, amifostine, aminoglutethimide, aminolevulinic acid, amrubicin, amsacrine, anastrozole, angiostatin, apremilast, aprepitant, arsenic trioxide, ascorbic acid, 1-asparaginase, azacitidine, azathioprine sodium, bazedoxifene (serm), belinostat, bendamustine hcl, O6-benzylguanine, bevacizumab, bexarotene, bicalutamide, biricodar, bleomycin sulfate, bortezomib, bosutinib, brivudine, buserelin, busulfan, buthionine sulfoxime, cabazitaxel, cabozantinib, capecitabine, carboplatin, carboquone, carfilzomib, carmofur, carmustine, ceritinib, chlorambucil, cisplatin, cladribine, clodronate disodium, clofarabine, crizotinib, cyclophosphamide, cyclosporine, cytarabine, cytosine arabinoside, dabrafenib, dacarbazine, dactinomycin, dasatinib, datinomycin, daunorubicin, decitabine, defribrotide, degarelix acetate, dexamethasone, dexrazoxane hydrochloride, diaziquone, diethyl stilbestrol, docetaxel, doxifluridine, doxorubicin hydrochloride, doxorubicin free base, dromostanolone propionate, dutasteride, eltrombopag, enzalutamide, epirubicin hydrochloride, eribulin mesylate, erlotinib hydrochloride, estramustine phosphate sodium, ethinyl estradiol, etoposide phosphate, etoposide, everolimus, exemestane, fentanyl, filgrastim, fingolimod, floxuridine, fludarabine phosphate, fluorouracil, fluoxymesterone, flutamide, formestane, formylmelphalan, fosaprepitant, fotemustine, fulvestrant, gefitinib, gemcitabine hydrochloride, gemcitabine free base, glutathione, glyciphosphoramide, glyfosfin, goserelin acetate, granisetron hydrochloride, heptaplatin, hexyl 5-aminolevulinate, histrelin acetate, hydroxyprogesterone caproate, hydroxyurea, ibandronate sodium, ibrutinib, icotinib, idarubicin HCl, idelalisib, idoxuridine, ifosfamide, interferon alpha, imatinib mesylate, imiquimod, ingenol mebutate, ipilimumab, irinotecan hydrochloride, ixabepilone, lanreotide acetate, lapatinib free base, lapatinib ditosylate, lasofoxifene, lenalidomide, letrozole, leucovorin calcium, leuprolide acetate, levamisole hydrochloride, levoleucovorin calcium, iobenguane, lobaplatin, lomustine, maropitant, masoprocol, mechlorethamine hydrochloride, megestrol acetate, medroxyprogesterone acetate, melphalan hydrochloride, mercaptopurine, mercaptoethane sulfonate sodium, methotrexate, methoxsalen, methyl aminolevulinate, methylene blue, methylisoindigotin, mifamurtide, miltefosine, miriplatin, mithamycin, mitobronitol, mitomycin C, mitotane, mitoxantrone hydrochloride, mycophenolate mofetil, nabiximols, nafarelin, nandrolone, nedaplatin, nelarabine, netupitant, nilotinib, nilutamide, nimustine, nintedanib, nocodazole, octreotide, olaparib, omacetaxine mepesuccinate, ondansetron hydrochloride, oxaliplatin, paclitaxel, palbociclib, palifermin, palonosetron hydrochloride, pamidronate disodium, panobinostat, pasireotide, pazopanib hydrochloride, pegfilrastim, pemetrexed disodium, pentostatin, peplomycin, pipobroman, pirarubicin, plerixafor, plicamycin, pomalidomide, ponatinib, porfimer sodium, porfiromycin, pralatrexate, prednimustine, prednisolone, prednisone, procarbazine hydrochloride, quinagolide hydrochloride, raloxifene, raltitrexed, radotinib, ranimustine, retinoic acids, revlimide, rituxinab, romidepsin, ruxolitinib, ruxolitinib phosphate, semustine, sirolimus, sodium thiosulfate, sorafenib free base, sorafenib tosylate, streptozocin, sufentanil, sunitinib, tacrolimus, talaporfin sodium, tamibarotene, tamoxifen citrate, tapentadol, temoporfin, temozolomide, temsirolimus, teniposide, teriflunomide, tertiposide, testolactone, testosterone propionate, thalidomide, thioguanine, thiotepa, thymalfasin, toceranib phosphate, topotecan hydrochloride, toremifene citrate, trabectedin, trametinib, tretinoin, trilostane, triptorelin, tropisetron, uramustine, valrubicin, vandetanib, vedotin, vemurafenib, verteporfin, vinblastine, vincristine sulfate, vincristine free base, vindesine, vinorelbine tartrate, vorinostat, and zoledronic acid.

A compound of Formula (6) or a pharmaceutical composition thereof may be administered in conjunction with one or more chemotherapeutic agents such as, for example, abemaciclib, abiraterone acetate, ABVD, ABVE, ABVE-PC, AC, acalabrutinib, AC-T, ADE, ado-trastuzumab emtansine, afatinib dimaleate, aldesleukin, alectinib, alemtuzumab, alpelisib, amifostine, aminolevulinic acid hydrochloride, anastrozole, apalutamide, aprepitant, arsenic trioxide, asparaginase Erwinia chrysanthemi, atezolizumab, avelumab, axicabtagene ciloleucel, axitinib, azacitidine, BEACOPP, belinostat, bendamustine hydrochloride, BEP, bevacizumab, bexarotene, bicalutamide, binimetinib, bleomycin sulfate, blinatumomab, bortezomib, bosutinib, brentuximab vedotin, brigatinib, BuMel, busulfan, cabazitaxel, cabozantinib-s-malate, CAF, calaspargase pegol-mknl, capecitabine, caplacizumab-yhdp, CAPDX, carboplatin, carboplatin-taxol, carfilzomib, carmustine, carmustine implant, CEM, cemiplimab-rwlc, ceritinib, cetuximab, CEV, chlorambucil, chlorambucil-prednisone, CHOP, cisplatin, cladribine, clofarabine, CMF, cobimetinib, copanlisib hydrochloride, COPDAC, COPP, COPP-ABV, crizotinib, CVP, cyclophosphamide, cytarabine, cytarabine liposome, dabrafenib mesylate, dacarbazine, dacomitinib, dactinomycin, daratumumab, darbepoetin a, dasatinib, daunorubicin hydrochloride, daunorubicin hydrochloride and cytarabine liposome, decitabine, defibrotide sodium, degarelix, denileukin diftitox, denosumab, dexamethasone, dexrazoxane hydrochloride, dinutuximab, docetaxel, doxorubicin hydrochloride, doxorubicin hydrochloride liposome, durvalumab, duvelisib, elotuzumab, eltrombopag olamine, emapalumab-lzsg, enasidenib mesylate, encorafenib, enzalutamide, epirubicin hydrochloride, EPOCH, epoetin a, erdafitinib, eribulin mesylate, erlotinib hydrochloride, etoposide, etoposide phosphate, everolimus, exemestane, fec, filgrastim, fludarabine phosphate, fluorouracil injection, fluorouracil—topical, flutamide, folfiri, folfiri-bevacizumab, folfiri-cetuximab, folfirinox, folfox, fostamatinib disodium, FU-LV, fulvestrant, gefitinib, gemcitabine hydrochloride, gemcitabine-cisplatin, gemcitabine-oxaliplatin, gemtuzumab ozogamicin, gilteritinib fumarate, glasdegib maleate, glucarpidase, goserelin acetate, granisetron, HPV bivalent vaccine, HPV bivalent vaccine, recombinant HPV nonavalent vaccine, HPV nonavalent vaccine, recombinant, HPV quadrivalent vaccine, HPV uadrivalent vaccine recombinant, hydroxyurea, hyper-CVAD, ibritumomab tiuxetan, ibrutinib, ICE, idarubicin hydrochloride, idelalisib, ifosfamide, imatinib mesylate, imiquimod, inotuzumab ozogamicin, interferon α-2b recombinant, iobenguane $^{131}$I, ipilimumab, irinotecan hydrochloride, irinotecan hydrochloride liposome, ivosidenib, ixabepilone, ixazomib citrate, JEB, lanreotide acetate, lapatinib ditosylate, larotrectinib sulfate, lenalidomide, lenvatinib mesylate, letrozole, leucovorin calcium, leuprolide acetate, lomustine, lorlatinib, lutetium Lu 177-dotatate, mechlorethamine hydrochloride, megestrol acetate, melphalan, melphalan hydrochloride, mercaptopurine, mesna, methotrexate, methylnaltrexone bromide, midostaurin, mitomycin c, mitoxantrone hydrochloride, mogamulizumab-kpkc, moxetumomab pasudotox-tdfk, MVAC, necitumumab, nelarabine, neratinib maleate, netupitant and palonosetron hydrochloride, nilotinib, nilutamide, niraparib tosylate monohydrate, nivolumab, obinutuzumab, OEPA, ofatumumab, OFF, olaparib, olaratumab, omacetaxine mepesuccinate, ondansetron hydrochloride, OPPA, osimertinib mesylate, oxaliplatin, paclitaxel, paclitaxel albumin-stabilized nanoparticle formulation, PAD, palbociclib, palifermin, palonosetron hydrochloride, palonosetron hydrochloride and netupitant, pamidronate disodium, panitumumab, panobinostat, pazopanib hydrochloride, PCV, PEB, pegaspargase, pegfilgrastim, peginterferon α-2b, pembrolizumab, pemetrexed disodium, pertuzumab, plerixafor, polatuzumab vedotin-piiq, pomalidomide, ponatinib hydrochloride, pralatrexate, prednisone, procarbazine hydrochloride, propranolol hydrochloride, radium 223 dichloride, raloxifene hydrochloride, ramucirumab, rasburicase, ravulizumab-cwvz, R-CHOP, R-CVP, recombinant HPV bivalent vaccine, recombinant HPV nonavalent vaccine, recombinant HPV quadrivalent vaccine, recombinant interferon α-2b, regorafenib, R-EPOCH, ribociclib, R-ICE, rituximab, rituximab and hyaluronidase human, rolapitant hydrochloride, romidepsin, romiplostim, rucaparib camsylate, ruxolitinib phosphate, siltuximab, sipuleucel-t, sonidegib, sorafenib tosylate, STANFORD V, sunitinib malate, TAC, tagraxofusp-erzs, talazoparib tosylate, talc, talimogene laherparepvec, tamoxifen citrate, temozolomide, temsirolimus, thalidomide, thioguanine, thiotepa, tisagenlecleucel, tocilizumab, topotecan hydrochloride, toremifene, TPF, trabectedin, trametinib, trastuzumab, trastuzumab and hyaluronidase-oysk, trifluridine and tipiracil hydrochloride, uridine triacetate, VAC, Valrubicin, VAMP, vandetanib, VeIP, vemurafenib, venetoclax, vinblastine sulfate, vincristine sulfate liposome, vinorelbine tartrate, vip, vismodegib, vorinostat, XELIRI, XELOX, Ziv-aflibercept, zoledronic acid, and combinations of any of the foregoing.

A compound provided by the present disclosure or a pharmaceutically acceptable salt thereof or a pharmaceutical composition thereof can be administered to a patient in conjunction with another compound known to be useful for treating the inflammatory disease, the autoimmune diseases, or the age-related disease being treated by the compound provided by the present disclosure.

The efficacy of administering a compound of Formula (6) or a pharmaceutical composition thereof for treating cancer, an inflammatory disease, or an autoimmune disease may be assessed using in vitro and animal studies and in clinical trials.

Methods of inhibiting p38α MAPK provided by the present disclosure include contacting p38α MAPK with a compound provided by the present disclosure to a pocket near the ED substrate-docking site of p38α MAPK.

Methods of inhibiting p38α MAPK provided by the present disclosure do not result in loss of p38α-dependent counterregulatory responses. The p38α-dependent counter-regulatory response relates to mitogen- and stress-activated protein kinase-I (MSK1), or MSK2. In targeting a pocket near the ED substrate-docking site of p38α, the inhibitors provided by the present disclosure avoid interfering with CD-specific substrates, including MSK1/2, thus limiting inflammation through expression of IL-10 and DUSP2.

ASPECTS OF THE INVENTION

Aspect 1. A compound having the structure of Formula (6):

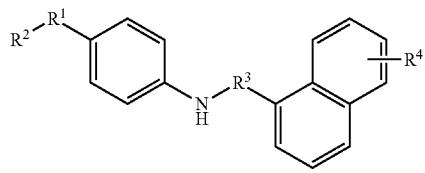

(6)

or a pharmaceutically acceptable salt thereof, wherein,
$R^1$ is selected from $C_{1-4}$ alkanediyl, $C_{1-4}$ heteroalkanediyl, substituted $C_{1-4}$ alkanediyl, and substituted $C_{1-4}$ heteroalkanediyl;

$R^2$ is substituted $C_{5-12}$ heterocycloalkyl;
$R^3$ is selected from —C(=O)— and —S(=O)$_2$—; and
$R^4$ is selected from —N(R$^5$)$_2$ wherein each R$^5$ is independently selected from hydrogen and $C_{1-4}$ alkyl.

Aspect 2. The compound of aspect 1, wherein each of the one or more substituents is independently selected from —OH, =O, —NH$_2$, —NO$_2$, $C_{1-6}$ alkyl, $C_{1-6}$ cycloalkyl, $C_6$ aryl, $C_{1-6}$ heteroalkyl, $C_{1-6}$ heterocycloalkyl, and $C_{5-6}$ heteroaryl.

Aspect 3. The compound of aspect 1, wherein each of the one or more substituents is independently selected from —OH, =O, —NH$_2$, —NO$_2$, $C_{1-3}$ alkyl, and $C_{1-3}$ heteroalkyl.

Aspect 4. The compound of aspect 1, wherein each of the one or more substituents is independently selected from —OH, =O, and $C_{1-3}$ alkyl.

Aspect 5. The compound of aspect 1, wherein each of the one or more substituents is =O.

Aspect 6. The compound of any one of aspects 1 to 5, wherein $R^1$ is $C_{1-4}$ alkanediyl.

Aspect 7. The compound of any one of aspects 1 to 5, wherein $R^1$ is ethanediyl.

Aspect 8. The compound of any one of aspects 1 to 5, wherein $R^1$ is methanediyl.

Aspect 9. The compound of any one of aspects 1 to 5, wherein $R^2$ is substituted $C_6$ heterocycloalkyl.

Aspect 10. The compound of aspect 9, wherein each of the one or more heteroatoms is independently selected from O and N.

Aspect 11. The compound of any one of aspects 1 to 10, wherein $R^2$ is morpholin-4-yl.

Aspect 12. The compound of any one of aspects 1 to 10, wherein $R^2$ is mono-substituted morpholin-4-yl.

Aspect 13. The compound of any one of aspects 1 to 10, wherein $R^2$ is 3-substituted morpholin-4-yl.

Aspect 14. The compound of any one of aspects 12 to 13, wherein each of the one or more substituents is independently selected from —OH, =O, —N(R$^5$)$_2$, wherein each R$^5$ is independently selected from hydrogen and $C_{1-3}$ alkyl.

Aspect 15. The compound of any one of aspects 12 to 13, wherein each of the one or more substituents is —OH, Aspect 16. The compound of any one of aspects 12 to 13, wherein each of the one or more substituents is =O.

Aspect 17. The compound of any one of aspects 12 to 13, wherein each of the one or more substituents is —N(R$^5$)$_2$, wherein each R$^5$ is independently selected from hydrogen and $C_{1-3}$ alkyl.

Aspect 18. The compound of any one of aspects 1 to 17, wherein $R^3$ is selected from —C(=O)— and —S(O)$_2$—.

Aspect 19. The compound of any one of aspects 1 to 17, wherein $R^3$ is —C(=O)—.

Aspect 20. The compound of any one of aspects 1 to 17, wherein $R^3$ is —S(O)$_2$—.

Aspect 21. The compound of any one of aspects 1 to 20, wherein $R^4$ is bonded to the 3-position, the 4-position, the 5-position, the 6-position, or the 7-position of the naphthyl moiety.

Aspect 22. The compound of any one of aspects 1 to 20, wherein $R^4$ is bonded to the 5-position of the naphthyl moiety.

Aspect 23. The compound of aspect 1, wherein,
$R^1$ is $C_{1-3}$ alkanediyl;
$R^2$ is substituted 4-morpholinyl;
$R^3$ is selected from —C(=O)— and —S(O)$_2$—; and
$R^4$ is selected from —N(R$^5$)$_2$ wherein each R$^5$ is independently selected from hydrogen and $C_{1-3}$ alkyl.

Aspect 24. The compound of aspect 1, wherein, $R^1$ is methane-diyl;
$R^2$ is substituted 4-morpholinyl;
$R^3$ is $-S(O)_2-$; and
$R^4$ is $-N(R^5)_2$ wherein each $R^5$ is independently selected from hydrogen and methyl.

Aspect 25. The compound of any one of aspects 23 to 24, wherein $R^2$ is 3-substituted 4-morpholinyl.

Aspect 26. The compound of any one of aspects 23 to 25, wherein in a moiety of $R^2$, the substituent is =O.

Aspect 27. The compound of any one of aspects 23 to 26, wherein $R^4$ is selected from $-NH(-CH_3)$ and $-N(-CH_3)_2$.

Aspect 28. The compound of aspect 1, wherein the compound is selected from:
4-amino-N-(4-((3-oxomorpholino)methyl)phenyl)naphthalene-1-sulfonamide;
4-(methylamino)-N-(4-((3-oxomorpholino)methyl)phenyl)naphthalene-1-sulfonamide;
4-(dimethylamino)-N-(4-((3-oxomorpholino)methyl)phenyl)naphthalene-1-sulfonamide;
5-amino-N-(4-((3-oxomorpholino)methyl)phenyl)naphthalene-1-sulfonamide;
5-(methylamino)-N-(4-((3-oxomorpholino)methyl)phenyl)naphthalene-1-sulfonamide;
5-(dimethylamino)-N-(4-((3-oxomorpholino)methyl)phenyl)naphthalene-1-sulfonamide;
6-amino-N-(4-((3-oxomorpholino)methyl)phenyl)naphthalene-1-sulfonamide;
6-(methylamino)-N-(4-((3-oxomorpholino)methyl)phenyl)naphthalene-1-sulfonamide; and
6-(dimethylamino)-N-(4-((3-oxomorpholino)methyl)phenyl)naphthalene-1-sulfonamide;
or a pharmaceutically acceptable salt of any of the foregoing.

Aspect 29. The compound of aspect 1, wherein the compound is 5-amino-N-(4-((3-oxomorpholino)methyl)phenyl)naphthalene-1-sulfonamide (Compound 5) or a pharmaceutically acceptable salt thereof:

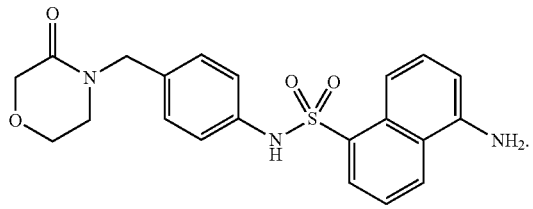 [SMILES: Nc1cccc2c(S(=O)(=O)Nc3ccc(CN4CCOCC4=O)cc3)cccc12]

Aspect 30. The compound of aspect 1, wherein the compound is 5-(methylamino)-N-(4-((3-oxomorpholino)methyl)phenyl)naphthalene-1-sulfonamide (2) or a pharmaceutically acceptable salt thereof:

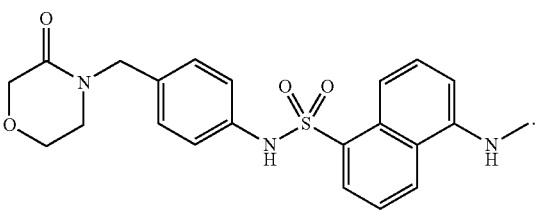

Aspect 31. The compound of aspect 1, wherein the compound is 5-(dimethylamino)-N-(4-((3-oxomorpholino)methyl)phenyl)naphthalene-1-sulfonamide (3) or a pharmaceutically acceptable salt thereof:

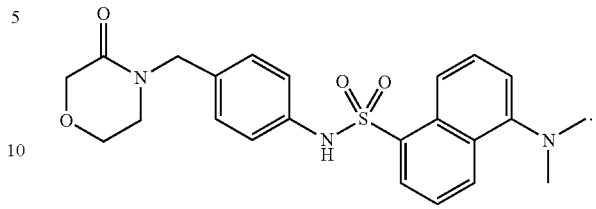

Aspect 32. The compound of any one of aspects 1 to 31, wherein the compound inhibits the p38α MAPK receptor.

Aspect 33. The compound of any one of aspects 1 to 32, wherein the compound selectively inhibits the p38α MAPK receptor.

Aspect 34. The compound of any one of aspects 1 to 33, wherein the compound has a higher binding affinity to the p38α MAPK subunit than to the p38β MAPK subunit.

Aspect 35. The compound of any one of aspects 1 to 34, wherein the compound binds to a selective binding site of p38α MAPK, wherein the binding pocket is defined by at least residues R49, H107, L108, and K165 of p38α MAPK.

Aspect 36. The compound of aspect 35, wherein the compound competitively binds to the selective binding site competitively with 4-chloro-N-(4-((1,1-dioxidothiomorpholino)methyl)phenyl)benzamide.

Aspect 37. The compound of any one of aspects 1 to 36, wherein the compound inhibits MK2 phosphorylation induced by 4-chloro-N-(4-((1,1-dioxidothiomorpholino)methyl)phenyl)benzamide in anisomycin-stimulated HeLa cells.

Aspect 38. A pharmaceutical composition comprising the compound of any one of aspects 1 to 37 or a pharmaceutically acceptable salt thereof.

Aspect 39. The pharmaceutical composition of aspect 38, wherein the pharmaceutical composition comprises a therapeutically effective amount of the compound of any one of aspects 1 to 37 or a pharmaceutically acceptable salt thereof for treating a disease in a patient.

Aspect 40. The pharmaceutical composition of aspect 39, wherein the disease is treated by inhibiting the p38α MAPK receptor.

Aspect 41. The pharmaceutical composition of aspect 39, wherein the disease is cancer.

Aspect 42. The pharmaceutical composition of aspect 39, wherein the disease is an inflammatory disease.

Aspect 43. The pharmaceutical composition of aspect 39, wherein the disease is an autoimmune disease.

Aspect 44. The pharmaceutical composition of aspect 39, wherein the disease is selected from acute lung injury, acute respiratory distress syndrome (ARDS), and chronic obstructive pulmonary disease (COPD).

Aspect 45. A method of treating a disease in a patient comprising administering to a patient in need of such treatment a therapeutically effective amount of the compound of any one of aspects 1 to 37 or a pharmaceutically acceptable salt thereof, wherein the disease is treated by inhibiting the p38α MAPK receptor.

Aspect 46. A method of treating a disease in a patient comprising administering to a patient in need of such treatment a therapeutically effective amount of the compound of any one of aspects 1 to 37 or a pharmaceutically acceptable salt thereof, wherein the disease is cancer.

Aspect 47. The method of aspect 46, wherein the cancer is selected from breast cancer and melanoma.

Aspect 48. A method of treating a disease in a patient comprising administering to a patient in need of such treatment a therapeutically effective amount of the compound of any one of aspects 1 to 37 or a pharmaceutically acceptable salt thereof, wherein the disease is an inflammatory disease.

Aspect 49. The method of aspect 48, wherein the inflammatory disease is selected from acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes, and rheumatoid arthritis.

Aspect 50. A method of treating a disease in a patient comprising administering to a patient in need of such treatment a therapeutically effective amount of the compound of any one of aspects 1 to 37 or a pharmaceutically acceptable salt thereof, wherein the disease is an autoimmune disease.

Aspect 51. The method of aspect 50, wherein the autoimmune disease is selected from lupus, graft-versus-host disease, hepatitis C-induced vasculitis, Type I diabetes, multiple sclerosis, spontaneous loss of pregnancy, an atopic disease, and an inflammatory bowel disease.

Aspect 52. A method of treating a disease in a patient comprising administering to a patient in need of such treatment a therapeutically effective amount of the compound of any one of aspects 1 to 37 or a pharmaceutically acceptable salt thereof, wherein the disease is an age-related disease.

Aspect 53. The method of aspect 52, wherein the age-related disease is selected from hearing loss, muscle degeneration, Werner's syndrome, cellular aging, and Alzheimer's disease.

Aspect 54. A method of treating a disease in a patient comprising administering to a patient in need of such treatment a therapeutically effective amount of the compound of any one of aspects 1 to 37 or a pharmaceutically acceptable salt thereof, wherein the disease is selected from acute lung injury, acute respiratory distress syndrome (ARDS), and chronic obstructive pulmonary disease (COPD).

Aspect 55. A method of inhibiting the p38α MAPK receptor comprising contacting the p38α MAPK receptor with the compound of any one of aspects 1 to 37 or a pharmaceutically acceptable salt thereof.

Aspect 56. A method of inhibiting the p38α MAPK receptor in a patient comprising administering to a patient a pharmacologically effective amount of the compound of any one of aspects 1 to 37 or a pharmaceutically acceptable salt thereof.

Aspect 57. The method of aspect 56, wherein inhibiting the p38α MAPK receptor comprises selectively inhibiting the p38α MAPK receptor.

Aspect 58. The method of aspect 57, wherein inhibiting the p38α MAPK receptor does not result in loss of a p38α-dependent counterregulatory response.

Aspect 59. The method of aspect 58, wherein the p38α-dependent counterregulatory response relates to mitogen- and stress-activated protein kinase-1 (MSK1) or MSK2.

Aspect 60. The method of any one of aspects 57 to 59, wherein selectively inhibiting the p38α MAPK receptor stabilizes an endothelial or epithelial barrier function.

Aspect 61. The method of any one of aspects 57 to 60, wherein selectively inhibiting the p38α MAPK receptor reduces inflammation.

Aspect 62. The method of any one of aspects 57 to 61, wherein selectively inhibiting the p38α MAPK receptor mitigates KPS-induced lung injury.

Aspect 63. The method of any one of aspects 57 to 62, wherein selectively inhibiting the p38α MAPK receptor regulates leukocyte trafficking.

Aspect 64. The method of any one of aspects 57 to 63, wherein selectively inhibiting the p38α MAPK receptor regulates cytokine expression.

EXAMPLES

The following examples describe in detail the synthesis of compounds of Formula (6), the characterization of compounds of Formula (6) and uses of compounds of Formula (6). It will be apparent to those skilled in the art that many modifications, both to materials and methods, may be practiced without departing from the scope of the disclosure.

Example 1

Synthesis of 5-(methylamino)-N-(4-(morpholinomethyl)phenyl)naphthalene-1-sulfonamide (1)

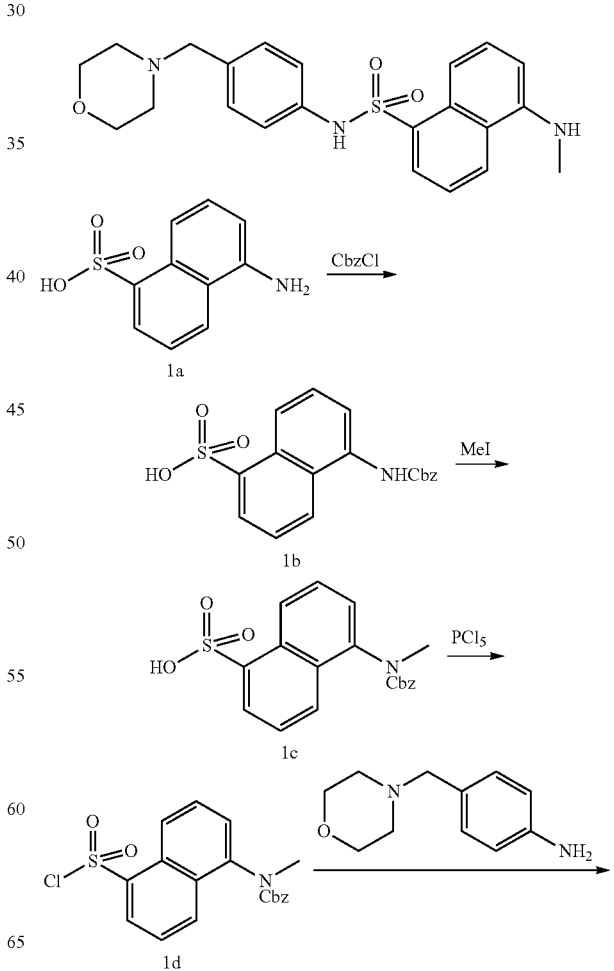

-continued

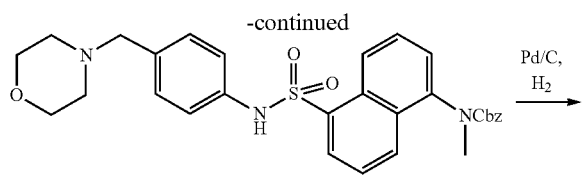

1e

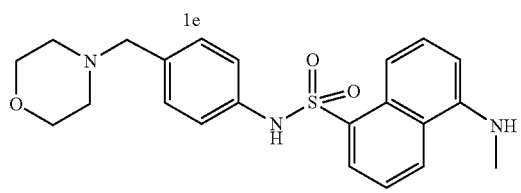

1e

Step 1: 5-(((Benzyloxy)carbonyl)amino)naphthalene-1-sulfonic acid (1b).

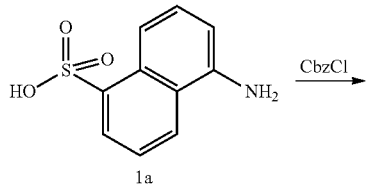

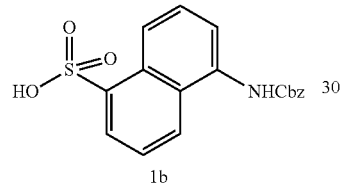

1b

To a solution of 5-aminonaphthalene-1-sulfonic acid (1a) (50.2 g, 0.2249 mol) in 0.1M NaHCO₃ (40 mL) was added 2M NaOH until the pH was adjusted to 10. Benzyl chloroformate (57.54 g, 0.3373 mol) was added to the stirred solution at 0° C. The temperature was raised to 25° C. and stirring was continued for 3 hours. LCMS showed a major peak as the target molecule. The reaction mixture was adjusted to pH 2 with 4M HCl, concentrated under reduced pressure, and purified by Biotage® Isolera One chromatography (C18 column, eluting with 10% to 95% MeCN/H₂O containing 0.1% HCOOH) to afford 5-(((benzyloxy)carbonyl)amino)naphthalene-1-sulfonic acid (1b) (30.5 g) as a purple solid. LCMS: m/z 355.9 [M+H]⁻.

Step 2: 5-5-(((Benzyloxy)carbonyl)(methyl)amino)naphthalene-1-sulfonic acid (1c).

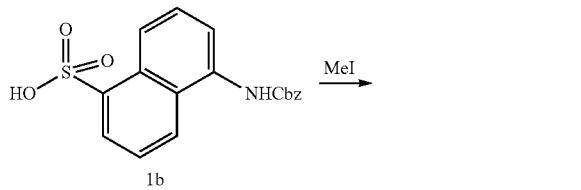

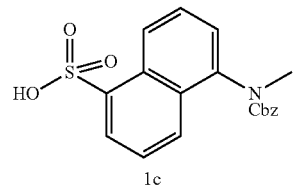

1c

To a solution of 5-(((benzyloxy)carbonyl)amino)naphthalene-1-sulfonic acid (1b) (30.5 g, 0.08534 mol) in dry DMF (300 mL) was added sodium hydride (60% in mineral oil, 4.5 g, 0.1109 mol) at 0° C. Upon completion of the addition, the reaction mixture was stirred at 0° C. for 30 minutes and iodomethane (15.7 g, 0.1109 mol) was added dropwise. Once the addition was complete, the resulting solution was stirred at 23° C. for 2 hours before being quenched with water. LCMS showed a major peak as the desired target molecule. The mixture was purified by Biotage® Isolera One chromatography (C18 column, eluting with 10% to 95% MeCN/H₂O containing 0.1% HCOOH) to afford 5(((benzyloxy)carbonyl)(methyl)amino)-naphthalene-1-sulfonic acid (1c) (12 g) as oil. LCMS: m/z 369.9 [M+H]⁻.

Step 3: Benzyl (5-(chlorosulfonyl)naphthalen-1-yl)(methyl)carbamate (1d).

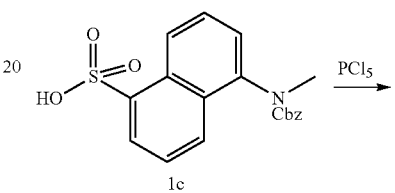

1c

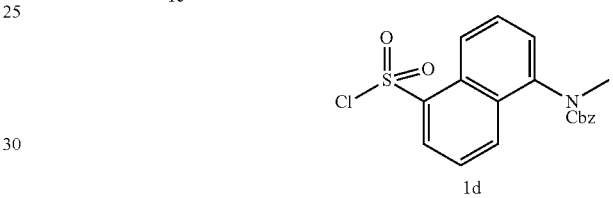

1d

A stirred mixture of 5-(((benzyloxy)carbonyl)(methyl)amino)naphthalene-1-sulfonic acid (1c) (12 g, 0.03231 mol) and PCl₅ (6.73 g, 0.03231 mol) in toluene (100 mL) was heated at 120° C. for 3 hours. TLC indicated a new spot was formed. The reaction mixture was allowed to cool to 23° C. and concentrated under vacuum and the result crude benzyl (5-(chlorosulfonyl)naphthalen-1-yl)(methyl)carbamate (1d), (16.17 g, about 80% purity on TLC) was used in the next step without further purification. LCMS: m/z 427.1 [M+H]⁺.

Step 4: Benzyl methyl(5-(N-(4-(morpholinomethyl)phenyl)sulfamoyl)naphthalen-1-yl)carbamate (1e).

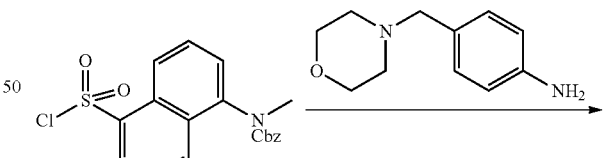

1d

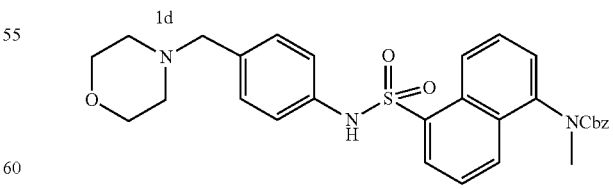

1e

To a stirred solution of 4-(morpholinomethyl)aniline (3.66 g, 0.01731 mol) in dichloromethane (60 mL) was added triethylamine (7.00 g, 0.06926 mol) at 0° C. After stirring at the same temperature for 30 min, benzyl (5-

(chlorosulfonyl)naphthalen-1-yl)(methyl)carbamate (1d) (6.75 g, 0.01731 mol) was added. The resulting solution was stirred at overnight at 45° C., allowed to cool to room temperature, and quenched with water. LCMS showed the major peak as the desired target molecule. The mixture was diluted with EtOAc, washed with water and saturated brine, dried with anhydrous sodium sulfate, filtered and concentrated under vacuum. The resulting crude product was purified by column chromatograph on silica gel (petroleum ether/ethyl acetate=10/1) to afford benzyl methyl(5-(N-(4-(morpholinomethyl)phenyl)sulfamoyl)naphthalen-1yl)-carbamate (1e), (4.6 g) as a yellow solid. LCMS: m/z 546.1 [M+H]$^+$.

Step 5: 5-(Methylamino)-N-(4-(morpholinomethyl)phenyl)naphthalene-1-sulfonamide (1).

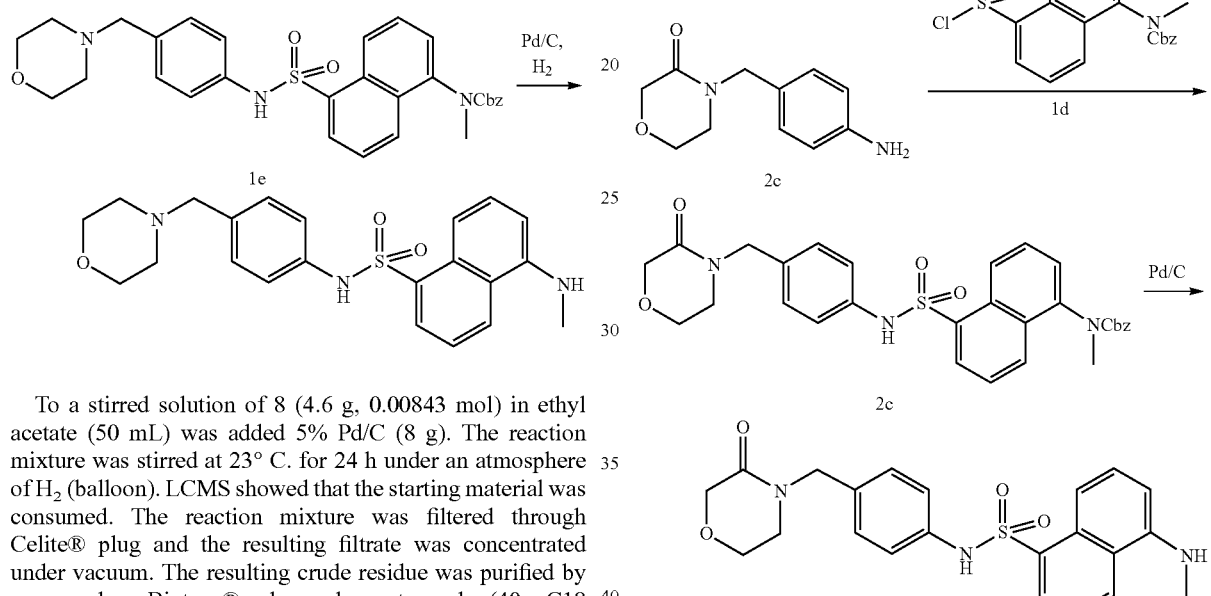

To a stirred solution of 8 (4.6 g, 0.00843 mol) in ethyl acetate (50 mL) was added 5% Pd/C (8 g). The reaction mixture was stirred at 23° C. for 24 h under an atmosphere of H$_2$ (balloon). LCMS showed that the starting material was consumed. The reaction mixture was filtered through Celite® plug and the resulting filtrate was concentrated under vacuum. The resulting crude residue was purified by reverse phase Biotage® column chromatography (40 g C18 column), ACN/water (0.1% HCOOH) 0-100%) to give 5-(methylamino)-N-(4-(morpholinomethyl)phenyl)naphthalene-1-sulfonamide of the title compound (1) (1.12 g) as a green-yellow solid. LCMS Rt=1.25 min; m/z calculated for [M+H]+412.0. $^1$H NMR (400 MHz, DMSO-d$_6$) δ 10.57 (s, 1H), 8.43 (d, J=8.5 Hz, 1H), 8.26-8.16 (m, 1H), 7.94 (d, J=8.6 Hz, 1H), 7.59-7.44 (m, 2H), 7.13 (s, 2H), 7.02 (s, 2H), 6.65 (d, J=4.9 Hz, 1H), 6.59 (d, J=7.8 Hz, 1H), 3.57 (s, 4H), 2.88 (d, J=4.6 Hz, 3H), 2.28 (s, 3H).

Example 2

Synthesis of 5-(Methylamino)-N-(4-((3-oxomorpholino)methyl)phenyl)naphthalene-1-sulfonamide (2)

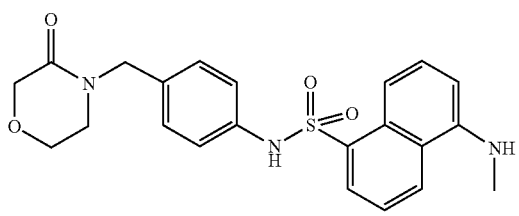

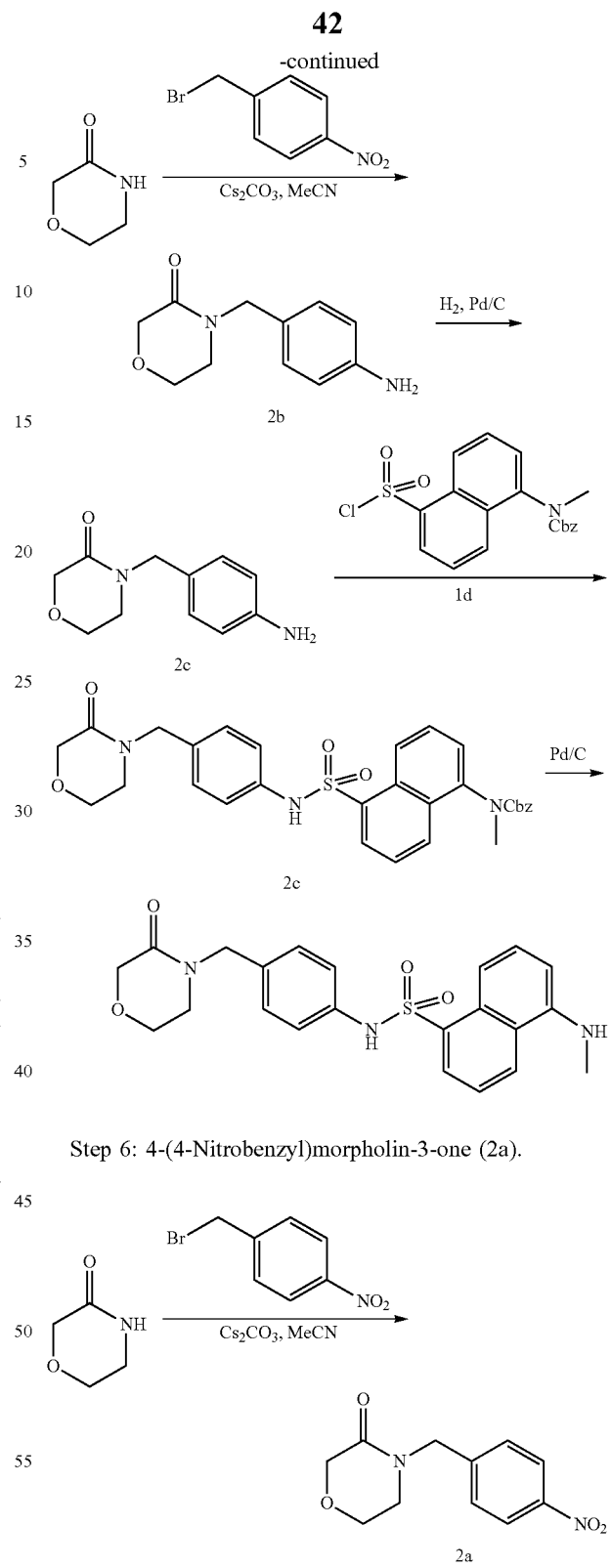

Step 6: 4-(4-Nitrobenzyl)morpholin-3-one (2a).

A stirred mixture of morpholin-3-one (20 g, 0.1978 mol), 1-(bromomethyl)-4-nitrobenzene (38.89 g, 0.1800 mol) and Cs$_2$CO$_3$ (116.65 g, 0.3580 mol) in acetonitrile (300 mL) was heated at 80° C. for 2 hours. The reaction mixture was allowed to cool to room temperature, filtered through a plug of Celite®, and the filtrate was concentrated under vacuum. The resulting crude product was purified by column chromatograph on silica gel (petroleum ether/ethyl acetate=1:1) to afford 4-(4-nitrobenzyl)morpholin-3-one (2a) (24.83 g) as a yellow solid. LCMS: m/z 237.1 [M+H]+.

Step 7: 4-(4-Aminobenzyl)morpholin-3-one (2b).

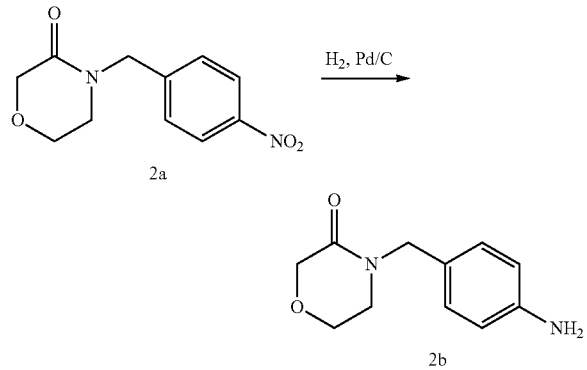

To a stirred solution of 4-(4-nitrobenzyl)morpholin-3-one (2b) (24.8 g, 0.1050 mol) in MeOH (5 mL) was added 10% Pd/C (6 g). The resulting mixture was stirred at room temperature for 1 hour under an atmosphere of H$_2$, (balloon). LCMS showed major peak was target molecule. The mixture was filtered through a bed of Celite® and the filtrate was concentrated under vacuum and the crude 4-(4-aminobenzyl)morpholin-3-one (2b) (18.4 g) was used in next step without any further purification. LCMS: m/z 207.1 [M+H]+.

Step 8: Benzyl methyl(5-(N-(4-((3-oxomorpholino)methyl)phenyl)sulfamoyl)naphthalen-1-yl)carbamate (2c).

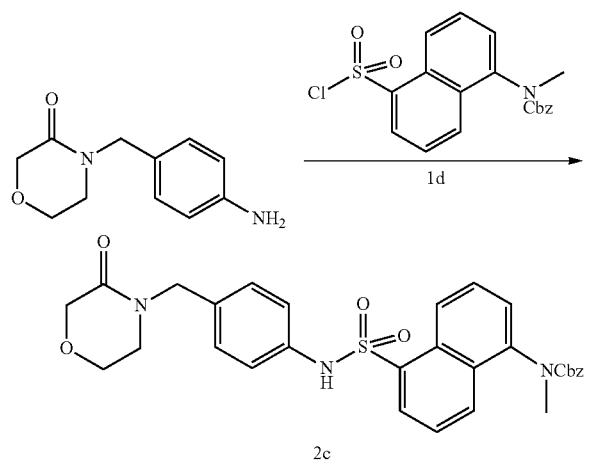

To a stirred solution of 4-(4-aminobenzyl)morpholin-3-one (2b) (4.53 g, 0.02196 mol) in dichloromethane (70 mL) at 0° C. was added triethylamine TEA (8.89 g, 0.02416 mol), maintaining the temperature at 0° C. during the course of the addition. Upon completion of the addition, the reaction mixture was stirred at 0° C. for an additional 30 min. Benzyl (5-(chlorosulfonyl)naphthalen-1-yl)(methyl)carbamate (1d) (9.42 g, 0.02416 mol) was added of the course of several minutes. The resulting solution was stirred at 45° C., overnight. The reaction mixture was allowed to cool to room temperature and quenched with H2O. LCMS showed major peak was target molecule. The mixture was diluted with EtOAc, washed with water and brine, dried over anhydrous Na$_2$SO$_4$, filtered and concentrated under vacuum. The resulting crude product was purified by column chromatograph on silica gel (petroleum ether/ethyl acetate=10/1) to afford benzyl methyl(5-(N-(4-((3-oxomorpholino)methyl)phenyl)-sulfamoyl)-naphthalen-1-yl)carbamate (2c) (5.3 g) as a yellow solid. LCMS: m/z 558.1 [M+H]−.

Step 9: 5-(Methylamino)-N-(4-((3-oxomorpholino)methyl)phenyl)naphthalene-1-sulfonamide (2).

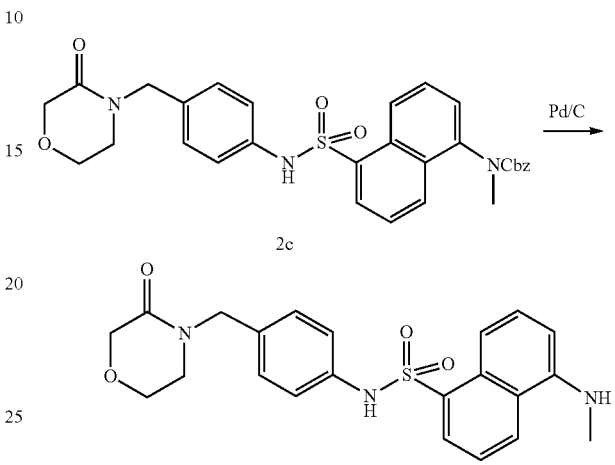

To a stirred solution of benzyl methyl(5-(N-(4-((3-oxomorpholino)methyl)phenyl)-sulfamoyl)-naphthalen-1-yl) carbamate (2c) (5.3 g, 9.47 mmol) in ethyl acetate (50 mL) was added 10% Pd/C (10 g). The mixture reaction was then stirred at 23° C. for 24 hours under H$_2$ (balloon). LCMS showed SM was consumed. The reaction was filtered through a plug of Celite and the resulting filtrate was concentrated under vacuum. The resulting crude residue was purified by Biotage® reverse phase-column chromatography (40 g C18 column), acetonitrile/H$_2$O (0.1% HCOOH) 0-100%) to give 5-(methylamino)-N-(4-((3-oxomorpholino)methyl)phenyl)-naphthalene-1-sulfonamide (2) (1.02 g) as a green-yellow solid. LCMS (Shimadzu 2020): Rt=1.81 min; m/z calculated for [M+H]+426.15. $^1$H NMR (400 MHz, DMSO-d$_6$) δ 10.53 (s, 1H), 8.36 (d, J=8.6 Hz, 1H), 8.13 (dd, J=7.4, 1.1 Hz, 1H), 7.87 (d, J=8.6 Hz, 1H), 7.50-7.39 (m, 2H), 7.00 (d, J=8.7 Hz, 2H), 6.98-6.92 (m, 2H), 6.58 (d, J=4.9 Hz, 1H), 6.52 (d, J=7.8 Hz, 1H), 4.32 (s, 2H), 4.01 (s, 2H), 3.71 (t, J=5.9, 4.4 Hz, 2H), 3.09 (t, J=5.9, 4.4 Hz, 2H), 2.81 (d, J=4.6 Hz, 3H).

Example 3

Synthesis of 5-(dimethylamino)-N-(4-((3-oxomorpholino)methyl)phenyl)naphthalene-1-sulfonamide (3)

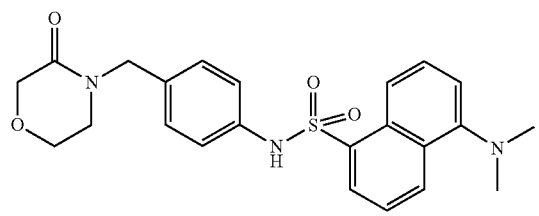

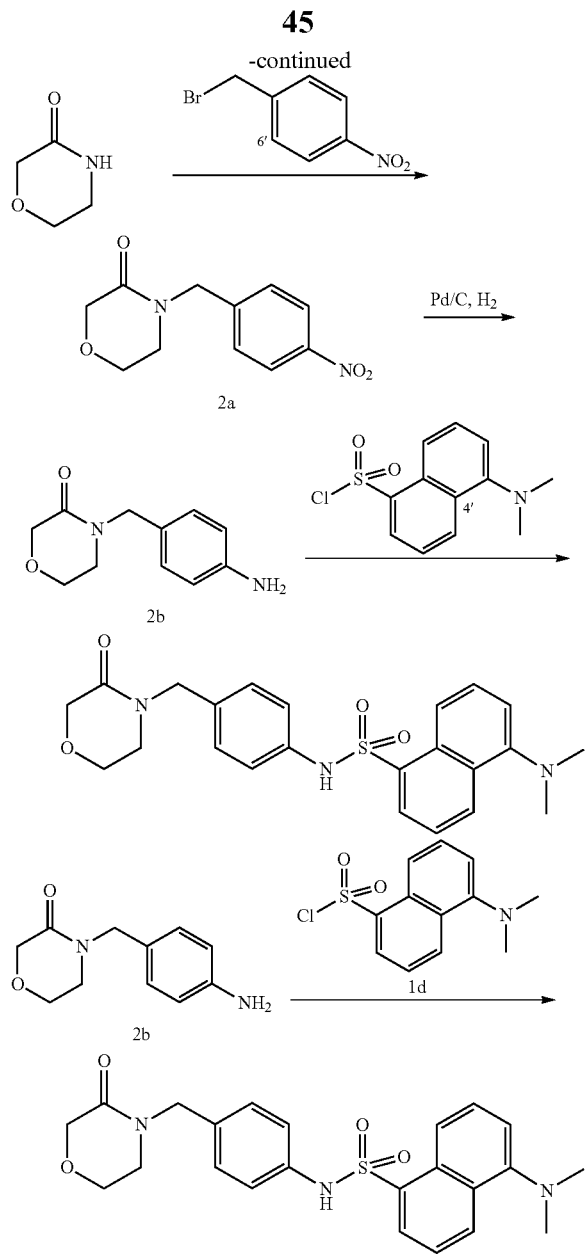

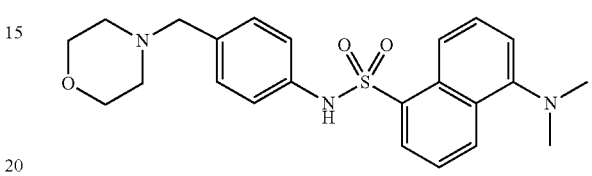

To a stirred solution of 4-(4-aminobenzyl)morpholin-3-one (2b) (7 g, 0.03394 mol) in dichloromethane (70 mL) at 0° C. was added TEA (13.74 g, 0.1358 mol), maintaining the reaction at 0° C. Upon completion of addition, the reaction mixture was stirred at 0° C. for 30 minutes. 5-(Dimethylamino)naphthalene-1-sulfonyl chloride (1d) (10.07 g, 0.03733 mol) was added over the course of a few minutes. The resulting solution was stirred overnight at 45° C. The reaction mixture was then allowed to cool to room temperature and quenched with water. LCMS showed the major peak as the desired target molecule. The mixture was diluted with EtOAc, washed with water and brine, dried over anhydrous $Na_2SO_4$, filtered and the resulting filtrate was concentrated under vacuum. The resulting crude product was purified by prep-HPLC (eluting with 30% to 100% $H_2O$/MeCN containing 0.1% HCOOH acid) and neutralized by 2M aqueous NaOH to afford 5-(dimethylamino)-N-(4-((3-oxomorpholino)methyl)phenyl)-naphthalene-1-sulfonamide (3) as a green solid. LCMS [M+H]+440.0. $^1$H NMR (400 MHz, DMSO-$d_6$) δ 10.66 (s, 1H), 8.44 (d, J=8.5 Hz, 1H), 8.35 (d, J=8.7 Hz, 1H), 8.21 (dd, J=7.4, 1.2 Hz, 1H), 7.60 (ddd, J=8.6, 7.5, 2.4 Hz, 2H), 7.25 (d, J=7.6 Hz, 1H), 7.05 (d, J=8.6 Hz, 2H), 7.00 (d, J=8.6 Hz, 2H), 4.36 (s, 2H), 4.04 (s, 2H), 3.73 (dd, J=5.9, 4.4 Hz, 2H), 3.12 (t, J=5.2 Hz, 2H), 2.80 (s, 6H).

Example 4

Synthesis of 5-(dimethylamino)-N-(4-(morpholinomethyl)phenyl)naphthalene-1-sulfonamide (4)

The synthesis of compound (4) is disclosed in Example 9 of U.S. Application Publication No. 2020/0331874 A1.

Example 5

Bioanalysis Procedures for Toxicology and Clinical Samples

The following methods are used for bioanalysis of samples for 2-week toxicology studies and clinical samples.

Bioanalysis of samples are performed according to a validated method. Monkey plasma samples are extracted by protein precipitation and analyzed by UPLC-MSMS using a Waters UPLC and API 5000® triple quadrupole mass spectrometer (AB Sciex, Toronto, Canada) with an ACE® Excel® 2 C18 column (50×3.0 mm, 2 μm particle size). Acquisition and chromatographic peak integration are performed using Analyst® Software 1.6.3 (AB Sciex). The peak areas for analytes and internal standard are imported into Watson LIMS® Software version 7.4.1 (Thermo Fisher Scientific, Philadelphia, USA) for standard curve regression analysis and quantification of analytes in the samples. All analytical instruments and software are validated using appropriate procedures.

Example 6

Bioanalysis Procedures for Non-GLP Pharmacokinetic Studies

The following methods are used for bioanalysis of samples for non-GLP pharmacokinetic studies.

Bioanalysis of samples are performed according to a validated method. Plasma samples are extracted by protein precipitation and analyzed by UPLC-MSMS using a Shimadzu UPLC and API 5000® triple quadrupole mass spectrometer (AB Sciex, Toronto, Canada), with a Waters Acquity UPLC BEH C18 column (50 mm×2.1 mm, 1.7 μm particle size). Acquisition and chromatographic peak integration are performed using Analyst® Software 1.6.3 (AB Sciex). The peak areas for analytes and internal standard are imported into Watson LIMS® Software, version 7.4.1 (Thermo Fisher Scientific, Philadelphia, USA) for standard curve regression analysis and quantification of analytes in the samples. All analytical instruments and software are validated using appropriate procedures.

Example 7 p38 MAPK Substrate Phosphorylation Profile

To assess whether a compound provided by the present disclosure selectively can inhibit phosphorylation consistent with its target. HeLa cells are pretreated for 30 min with 10 µM SB203580, 50 µM test compound, or 0.1% DMSO vehicle control, then with the p38 activator, anisomycin (25 µg/mL) and phosphorylated test compound and Stat-I are analyzed by immunoblotting.

Example 8

Specific Binding to p38α MAPK

DSF is used to analyze concentration-specific binding of a compound of Formula (6) to p38α MAPK and p38β APK. To confirm that the test compound binds the CADD-targeted pocket, DSF is used to compare compound binding and SB203580-binding to wild-type p38α MAPK and a p38α MAPK mutant with four of the ten target pocket amino acids (R49K/HL107-8TF/KI65R) substituted. The mutant can exhibit SB203580-binding that was identical to wild-type p38α MAPK, but not test compound-binding.

Selective binding of test compound to the CADD-targeted pocket in p38α MAPK is confirmed using Saturation Transfer.

Example 9

Pharmacokinetics

The pharmacokinetics of Compounds (1)-(4) was determined in mice, rats, and monkeys.

Mouse Study.

Female CD-1 mice (n=9) received a single intraperitoneal dose of 1 mg/mouse of Compound (4). The dosing formulation was prepared prior to dose, with 2 mg/mL of Compound (4) in 4% DMSO and 96% PBS. Blood samples were collected from the mice at designated timepoints. Following collection, samples were centrifuged (2500 rpm for 10 minutes at 4° C.) and the resulting plasma was recovered and stored frozen (−60° C.).

Bioanalysis of the plasma samples was performed for Compounds (1)-(4). Mouse plasma samples were extracted by protein precipitation and analyzed by UPLC-MSMS using a Waters UPLC and API 5000® triple quadrupole mass spectrometer (AB Sciex, Toronto, Canada) with a Waters Acquity® UPLC BEH C18 column (50 mm×2.1 mm, 1.7 µm particle size). Acquisition and chromatographic peak integration were performed using Analyst® 1.7 Software. The standard curve regression and quantification of analytes in the samples was performed using the Analyst® Software.

Pharmacokinetic parameters were calculated based on the plasma concentration data for Compound (4) and the metabolites Compound (1)-(3) by non-compartmental methods using WinNonlin® Software, version 8.1 (Certara®, Inc). The area under the concentration time curve ($AUC_{inf}$) was calculated for Compounds (1)-(4). The percent $AUC_{inf}$ (% $AUC_{inf}$) for each metabolite was calculated as the ratio of the $AUC_{inf}$ for each respective metabolite divided by the $AUC_{inf}$ for Compound (4).

Rat Study.

Male Sprague-Dawley rats (n=3) received a single intravenous bolus dose of 10 mg/kg Compound (4). The dosing formulation was prepared by prior to dosing, with 5 mg/mL of Compound (4) in 14% sulphobutylether-β-cyclodextrin (SBECD) in deionized water (w/v). Blood samples were collected from each rat at designated timepoints. Following collection, the samples were centrifuged (2500 rpm for 10 minutes at approximately 4° C.) and the resulting plasma was recovered and stored frozen (−60° C.).

Bioanalysis of the samples was performed for Compounds (1)-(4). Rat plasma samples were extracted by protein precipitation and analyzed by UPLC-MSMS using a Waters UPLC and API 5000® triple quadrupole mass spectrometer (AB Sciex, Toronto, Canada) with a Waters Acquity® UPLC BEH C18 column (50 mm×2.1 mm, 1.7 µm particle size). Acquisition and chromatographic peak integration were performed using Analyst® 1.7 Software. The standard curve regression and quantification of analytes in the samples was performed using the Analyst® Software.

Pharmacokinetic parameters were calculated from the plasma concentration data for Compound (4) and the metabolites Compounds (1)-(3) by non-compartmental methods using WinNonlin® Software, version 8.1 (Certara®, Inc). The area under the concentration time curve ($AUC_{inf}$) was calculated for Compounds (1)-(4). The percent $AUC_{inf}$ for the metabolites was calculated as the ratio of the $AUC_{inf}$ for each respective metabolite divided by the $AUC_{inf}$ for Compound (4).

Monkey Study:

Male cynomolgus monkeys (n=3) received a single intravenous infusion over a period of 2 hours at a dose of 5 mg/kg Compound (4) (2.5 mL/kg/hour). The dosing formulation was prepared prior to dose, with 1 mg/mL of Compound (4) in 14% sulphobutylether-β-cyclodextrin (SBECD) in deionized water (w/v). Blood samples were collected from each monkey at designated timepoints. Following collection, the samples were centrifuged (2500 rpm for 10 minutes at 4° C.) and the resulting plasma was recovered and stored frozen (−60° C.).

Bioanalysis of samples was performed for Compounds (1)-(4). The monkey plasma samples were extracted by protein precipitation and analyzed by UPLC-MSMS using a Waters UPLC and API 5000® triple quadrupole mass spectrometer (AB Sciex, Toronto, Canada) with an ACE® Excel® 2 C18 column (50 mm×3.0 mm, 2 um particle size) or a Waters Acquity® UPLC BEH C18 column (50 mm×2.1 mm, 1.7 µm). Acquisition and chromatographic peak integration were performed using Analyst® Software, version 1.6.3. The standard curve regression and quantification of analytes in the samples was performed using Watson LIMS® Software, version 7.4.1 (Thermo Fisher Scientific, Philadelphia, USA) or the Analyst® Software.

Pharmacokinetic parameters were calculated from plasma concentration data for Compound (4) and its metabolites by non-compartmental methods using WinNonlin® Software, version 8.1 (Certara®, Inc). The area under the concentration time curve ($AUC_{inf}$) was calculated for Compounds (1)-(4). The percent $AUC_{inf}$ for each of the metabolites was calculated as the ratio of the $AUC_{inf}$ of each respective metabolite divided by the $AUC_{inf}$ of Compound (4).

Following oral administration of compound (2) to a mammal, the metabolites having the structure of Formula (1), (2) or (3) exhibited a % $AUC_{inf}$ (100×$AUC_{metabolite}$/$AUC_{Compound\ (4)}$) with respect to compound (4) as shown in Table 1.

TABLE 1

% AUC of in vivo metabolites of Compound (4).

| Metabolite | % AUC$_{inf}$ | | |
| --- | --- | --- | --- |
| | Mouse | Rat | Monkey |
| Compound (1) | 31 | 9 | 64 |
| Compound (2) | 10 | 48 | 132 |
| Compound (3) | 9 | 11 | 7 |

Example 10

Antiviral Effects in a SARS-CoV-2 Infected Cell Line

A549-ACE2 cells (Institut Pasteur, Paris, France) were cultured in DMEM (Corning) supplemented with 10% FBS (Peak Serum) and maintained at 37° C. with 5% $CO_2$. HEK293T-ACE2 cells (ATCC, CRL-3216) were maintained in DMEM (Corning) supplemented with 10% FB (Peak Serum) and Penicillin/Streptomycin (Corning) at 37° C. and 5% $CO_2$. hACE2 ectopically expressed cells were generated by transducing with a lentiviral vector expressing human ACE2. Puromycin resistant cells with hACE2 surface expression were sorted after staining with AlexaFluor 647-conjugated goat anti-hACE2 antibodies. Cells were then single-cell-cloned and screened for their ability to support SARS-CoV-2 replication. All cell lines used were regularly screened for mycoplasma contamination using a Universal Mycoplasma Detection Kit (ATCC, 30-1012K).

The SARS-CoV-2 isolate BetaCoV/France/IDF0372/2020 was supplied by the National Reference Centre for Respiratory Viruses hosted by Institut Pasteur (Paris, France). The isolate originated from a human sample. The isolate was supplied through the European Virus Archive goes Global (EVAg) platform. Viral stocks were prepared by propagation in Vero E6 cells in DMEM supplemented with 2% FBS. Viral titers were determined by plaque assay in Minimum Essential Media (MEM) supplemented with 2% (v/v) FBS (Invitrogen) and 0.05% agarose.

All experiments involving live SARS-CoV-2 were performed in compliance with the Institut Pasteur Paris guidelines for Biosafety Level 3 (BSL-3) Containment Procedures in Approved Laboratories.

Two hours before infection, the medium was replaced with DMEM (2% FBS) containing the compound of interest at concentrations 50% greater than those indicated, including a DMSO control. Plates were then transferred into the BSL-3 facility and the same volume of SARS-CoV-2 was added in DMEM (2% FBS), bringing the final compound concentration to the desired concentration. Plates were then incubated for 48 hours at 37° C.15% $CO_2$. All assays were performed in biologically independent triplicates.

Detection of viral genomes was performed by RT-qPCR, directly from the inactivated supernatant. SARS-CoV-2 specific primers targeting the N gene region: 5'-TAATCAGACAAGGAACTGATTA-3' (SEQ ID NO: 1) (Forward) and 5'-CGAAGGTGTGACTTCCATG-3' (SEQ ID NO: 2) (Reverse) were used with the Luna® Universal One-Step RT-qPCR Kit (NEB) in an Applied Biosystems QuantStudio® 7 thermocycler, with the following cycling conditions: 55° C. for 10 minutes, 95° C. for 1 minute, and 40 cycles of 95° C. for 10 s, followed by 60° C. for 1 minute. The number of viral genomes is expressed as PFU equivalents/mL and was calculated by performing a standard curve with RNA derived from a viral stock with a known viral titer.

Cell viability was measured using the CellTiter® Glo luminescent cell viability assay (Promega) following the manufacturer's instructions, and luminescence measured in a Tecan Infinite® 2000 plate reader. Cytotoxicity was performed in uninfected cells with same compound dilutions and concurrent with viral replication assay. Percent viability was calculated relative to untreated cells (100% viability) and cells lysed with 20% ethanol (0% viability).

A Hill function was fit to each dose response curve using the lsqcurvefit function in MATLAB (R2018a). IC50 (virus) values were defined as the concentration at which the percent measure (virus or cell viability quantification) crossed the 50% mark. If the fit curve did not begin above 50% and cross to below 50% throughout the dose response, an IC50 value was marked as greater than the maximum tested concentration.

Figure 2:
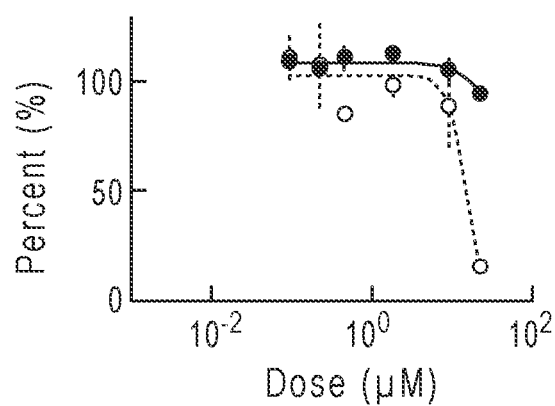
FIG. 2 shows the cell viability (black) and IC$_{50}$ (red) curves for a SARS-CoV-2 cell line treated with Compound (1).
Figure 3:
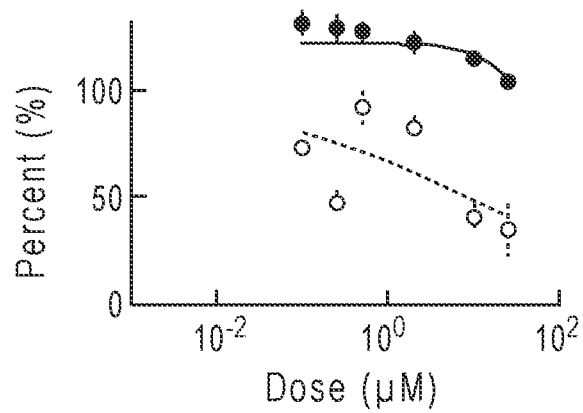
FIG. 3 shows the cell viability (black) and IC$_{50}$ (red) curves for a SARS-CoV-2 cell line treated with Compound (2).

The cell viability (black) and IC50 (red) curves in a SARS-CoV-2 cell line treated with compounds (4), (1), or (2) is shown in FIGS. 1-3, respectively.

Finally, it should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

What is claimed is:

1. A compound having the structure of Formula (6):

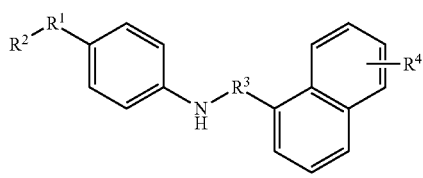
(6)

or a pharmaceutically acceptable salt thereof, wherein,
- $R^1$ is selected from $C_{1-4}$ alkanediyl, $C_{1-4}$ heteroalkanediyl, substituted $C_{1-4}$ alkanediyl, and substituted $C_{1-4}$ heteroalkanediyl;
- $R^2$ is substituted morpholin-4-yl;
- $R^3$ is selected from —C(=O)— and —S(=O)$_2$—; and
- $R^4$ is —N($R^5$)$_2$ wherein each $R^5$ is independently selected from hydrogen and $C_{1-4}$ alkyl,
- wherein each substituent is independently selected from —OH, =O, —NH$_2$, —NO$_2$, $C_{1-6}$ alkyl, $C_{1-6}$ cycloalkyl, $C_6$ aryl, $C_{1-6}$ heteroalkyl, $C_{1-6}$ heterocycloalkyl, and $C_{5-6}$ heteroaryl.

2. The compound of claim 1, wherein $R^1$ is $C_{1-4}$ alkanediyl.

3. The compound of claim 1, wherein $R^2$ is mono-substituted morpholin-4-yl.

4. The compound of claim 1, wherein $R^2$ is 3-substituted morpholin-4-yl.

5. The compound of claim 4, wherein each substituent is independently selected from —OH, =O, and —NH$_2$.

6. The compound of claim 3, wherein each substituent is =O.

7. The compound of claim 1, wherein $R^3$ is —S(O)$_2$—.

8. The compound of claim 1, wherein $R^4$ is bonded to the 5-position of the naphthyl moiety.

9. The compound of claim 1, wherein,
- $R^1$ is methane-diyl;
- $R^3$ is —S(O)$_2$—; and
- $R^4$ is —N($R^5$)$_2$ wherein each $R^5$ is independently selected from hydrogen and methyl.

10. The compound of claim 9, wherein $R^2$ is 3-substituted 4-morpholinyl.

11. The compound of claim 9, wherein in the moiety of $R^2$, the substituent is =O.

12. The compound of claim 1, wherein the compound is selected from:
- 4-amino-N-(4-((3-oxomorpholino)methyl)phenyl)naphthalene-1-sulfonamide;
- 4-(methylamino)-N-(4-((3-oxomorpholino)methyl)phenyl)naphthalene-1-sulfonamide;
- 4-(dimethylamino)-N-(4-((3-oxomorpholino)methyl)phenyl)naphthalene-1-sulfonamide;
- 5-amino-N-(4-((3-oxomorpholino)methyl)phenyl)naphthalene-1-sulfonamide;
- 5-(methylamino)-N-(4-((3-oxomorpholino)methyl)phenyl)naphthalene-1-sulfonamide;
- 5-(dimethylamino)-N-(4-((3-oxomorpholino)methyl)phenyl)naphthalene-1-sulfonamide;
- 6-amino-N-(4-((3-oxomorpholino)methyl)phenyl)naphthalene-1-sulfonamide;
- 6-(methylamino)-N-(4-((3-oxomorpholino)methyl)phenyl)naphthalene-1-sulfonamide; and
- 6-(dimethylamino)-N-(4-((3-oxomorpholino)methyl)phenyl)naphthalene-1-sulfonamide;
- or a pharmaceutically acceptable salt of any of the foregoing.

13. The compound of claim 1, wherein the compound is 5-amino-N-(4-((3-oxomorpholino)methyl)phenyl)naphthalene-1-sulfonamide (5) or a pharmaceutically acceptable salt thereof:

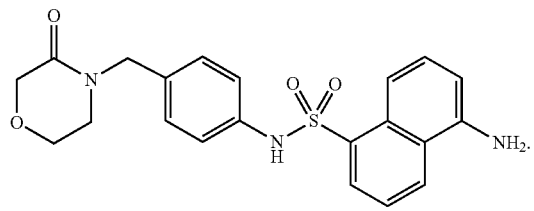

14. The compound of claim 1, wherein the compound is 5-(methylamino)-N-(4-((3-oxomorpholino)methyl)phenyl)naphthalene-1-sulfonamide (2) or a pharmaceutically acceptable salt thereof:

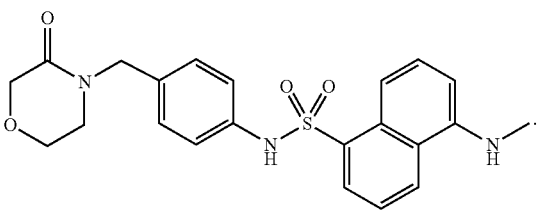 [SMILES: CNc1cccc2c(S(=O)(=O)Nc3ccc(CN4CCOCC4=O)cc3)cccc12]

15. The compound of claim 1, wherein the compound is 5-(dimethylamino)-N-(4-((3-oxomorpholino)methyl)phenyl)naphthalene-1-sulfonamide (3) or a pharmaceutically acceptable salt thereof:

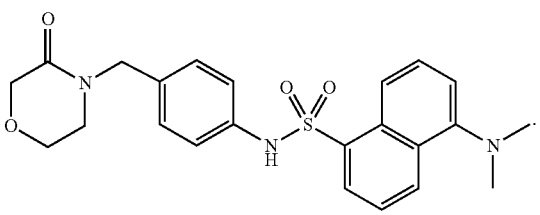

16. A pharmaceutical composition comprising the compound of claim 1 or a pharmaceutically acceptable salt thereof.

17. A method of treating a disease in a patient comprising administering to a patient in need of such treatment a therapeutically effective amount of the compound of claim 1 or a pharmaceutically acceptable salt thereof, wherein the disease is treated by inhibiting the p38α MAPK receptor.

18. A method of treating a disease in a patient comprising administering to a patient in need of such treatment a therapeutically effective amount of the compound of claim 1 or a pharmaceutically acceptable salt thereof, wherein the disease is cancer, wherein the cancer is selected from breast cancer and melanoma.

19. A method of treating a disease in a patient comprising administering to a patient in need of such treatment a therapeutically effective amount of the compound of claim 1 or a pharmaceutically acceptable salt thereof, wherein the disease is an inflammatory disease, wherein the inflammatory disease is selected from acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes, and rheumatoid arthritis.

20. A method of treating a disease in a patient comprising administering to a patient in need of such treatment a therapeutically effective amount of the compound of claim 1 or a pharmaceutically acceptable salt thereof, wherein the disease is an autoimmune disease, wherein the autoimmune disease is selected from lupus, graft-versus-host disease, hepatitis C-induced vasculitis, Type I diabetes, multiple sclerosis, spontaneous loss of pregnancy, an atopic disease, and an inflammatory bowel disease.

21. A method of treating a disease in a patient comprising administering to a patient in need of such treatment a therapeutically effective amount of the compound of claim 1 or a pharmaceutically acceptable salt thereof, wherein the disease is an age-related disease, wherein the age-related disease is selected from hearing loss, muscle degeneration, Werner's syndrome, cellular aging, and Alzheimer's disease.

22. A method of treating a disease in a patient comprising administering to a patient in need of such treatment a therapeutically effective amount of the compound of claim 1 or a pharmaceutically acceptable salt thereof, wherein the disease is selected from acute lung injury, acute respiratory distress syndrome (ARDS), and chronic obstructive pulmonary disease (COPD).

* * * * *

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
taatcagaca aggaactgat ta                                              22

<210> SEQ ID NO 2
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 2
cgaaggtgtg acttccatg                                              19
```